(12) United States Patent
Suzuki et al.

(10) Patent No.: US 9,644,193 B2
(45) Date of Patent: May 9, 2017

(54) B-1,3-GLUCANASE, POLYNUCLEOTIDE, RECOMBINANT VECTOR, TRANSFORMANT, PRODUCTION METHOD FOR B-1,3- GLUCANASE, ENZYME PREPARATION, AND PRODUCTION METHOD FOR PARAMYLON HAVING REDUCED MOLECULAR WEIGHT

(71) Applicant: Euglena Co., Ltd., Tokyo (JP)

(72) Inventors: Kengo Suzuki, Yokohama (JP); Ryo Arashida, Yokohama (JP); Yuka Marukawa, Yokohama (JP); Eriko Yoshida, Yokohama (JP); Takumi Takeda, Kitakami (JP); Yuki Nakano, Kitakami (JP); Naotake Konno, Kitakami (JP); Machiko Takahashi, Kitakami (JP)

(73) Assignee: Euglena Co., Ltd., Tokyo (JP)

( * ) Notice: Subject to any disclaimer, the term of this patent is extended or adjusted under 35 U.S.C. 154(b) by 0 days.

(21) Appl. No.: 14/909,211

(22) PCT Filed: Aug. 4, 2014

(86) PCT No.: PCT/JP2014/070459
§ 371 (c)(1),
(2) Date: Feb. 1, 2016

(87) PCT Pub. No.: WO2015/016375
PCT Pub. Date: Feb. 5, 2015

(65) Prior Publication Data
US 2016/0186153 A1  Jun. 30, 2016

(30) Foreign Application Priority Data

Aug. 2, 2013 (JP) ................................. 2013-161588
Sep. 5, 2013 (JP) ................................. 2013-184351

(51) Int. Cl.
| | |
|---|---|
| *C12N 9/26* | (2006.01) |
| *C12N 15/00* | (2006.01) |
| *C12P 19/14* | (2006.01) |
| *C12P 21/06* | (2006.01) |
| *C12P 21/04* | (2006.01) |
| *C07H 21/04* | (2006.01) |
| *C12N 9/42* | (2006.01) |
| *C12N 9/24* | (2006.01) |
| *A23K 20/189* | (2016.01) |
| *C12P 19/12* | (2006.01) |

(52) U.S. Cl.
CPC ............ *C12N 9/244* (2013.01); *A23K 20/189* (2016.05); *C12N 9/2405* (2013.01); *C12P 19/12* (2013.01); *C12P 19/14* (2013.01); *C12Y 302/01039* (2013.01); *C12Y 302/01006* (2013.01)

(58) Field of Classification Search
CPC ........ C12N 9/2405; C12N 9/244; C12P 19/14
See application file for complete search history.

(56) References Cited

U.S. PATENT DOCUMENTS

| 5,084,386 A | 1/1992 | Tusé et al. |
| 5,385,832 A | 1/1995 | Tusé et al. |
| 5,401,647 A | 3/1995 | Tanaka et al. |

FOREIGN PATENT DOCUMENTS

| EP | 0417254 B1 | 5/1995 |
| JP | 3-227939 A | 10/1991 |
| JP | 10-507078 A | 7/1998 |
| JP | 2003-529538 A | 10/2003 |
| JP | 2005-34146 A | 2/2005 |
| JP | 2005-224230 A | 8/2005 |

OTHER PUBLICATIONS

Branden et al. Introduction to Protein Structure, Garland Publishing Inc., New York, p. 247, 1991.*
Linthorst. Analysis of gene families encoding acidic and basic beta-1,3-glucanases of tobacco. Proc. Natl. Acad. Sci. U.S.A. 87, 8756-8760, 1990.*
Vogel et al., "Degradation of Paramylon by Euglena gracilis," J. Protozool, 1968, vol. 15, No. 4, pp. 657-662.
Barras, et al., "β-I,3-Glucan Hydrolases From Euglen A Gracilis; I. The Nature of the Hydrolases," Biochimica et Biophysica Acta, 1969, vol. 191, pp. 329-341.
Barras, et al., "β-I,3-Glucan Hydrolases From Euglen A Gracilis; II. Purification and Properties of the β-I,3-Glucan Exo-Hydrolase," Biochimica et Biophysica Acta, 1969, vol. 191, pp. 342-353.
Fellio J., "Laminarase of Euglena gracills," Science, 1960, vol. 131, p. 832 (total 2 pages).
International Preliminary Report on Patentability for PCT/JP2014/070459 dated Oct. 28, 2014.
Communication dated Jun. 9, 2015 from Japanese Patent Office in counterpart Application No. 2015-514700.
Communication dated Feb. 1, 2016 from U.S. Patent & Trademark Office in counterpart U.S. Appl. No. 14/909,211.
J. Peumans et al: "Purification, characterization and structural analysis of an abundant β-1, 3-glucanase from banana fruit."; Eur. J. Biochem. 267 (2000) pp. 1188-1195.
Communication dated Sep. 20, 2016, from the State Intellectual Property Office of People's Republic of China in counterpart Application No. 201480043070.3.
Communication dated Jun. 22, 2016 from the German Patent and Trademark Office in counterpart application No. 112014003580.7.
Database entry ENA EC682238.1; "High light non-normalized long fraction Euglena gracillis cDNA, mRNA sequence," (Jul. 1, 2006) 1 page total.
Database entry ENA EC682755.1; "High light non-normalized long fraction Euglena gracilis cDNA, mRNA sequence," (Jul. 1, 2006) 1 page total.

\* cited by examiner

*Primary Examiner* — Yong Pak
(74) *Attorney, Agent, or Firm* — Sughrue Mion, PLLC

(57) ABSTRACT

A β-1,3-glucanase that exhibits decomposition activity with respect to paramylon derived from the genus *Euglena*. The β-1,3-glucanase is derived from the genus *Euglena* and exhibits the properties indicated below: (1) effect: hydrolyzing the β-1,3-bond of β-1,3-glucan; and (2) substrate specificity: decomposing at least paramylon. The β-1,3-glucanase additionally exhibits the properties indicated below: (3) decomposition activity: the ratio of paramylon decomposition activity with respect to laminarin decomposition activity is 20% or higher; (4) optimum pH: 3.7-7.0; and (5) optimum temperature: 30-70° C.

7 Claims, 20 Drawing Sheets

SEPARATION OF LAMINARIN DECOMPOSITION ACTIVITY FRACTIONS BY HYDROPHOBIC COLUMN

SEPARATION OF LAMINARIN DECOMPOSITION
ACTIVITY FRACTIONS BY GEL FILTRATION COLUMN

SEPARATION OF LAMINARIN DECOMPOSITION
ACTIVITY FRACTIONS BY ANION-EXCHANGE COLUMN

SDS-PAGE OF
PARTIALLY PURIFIED PROTEIN

FIG. 10

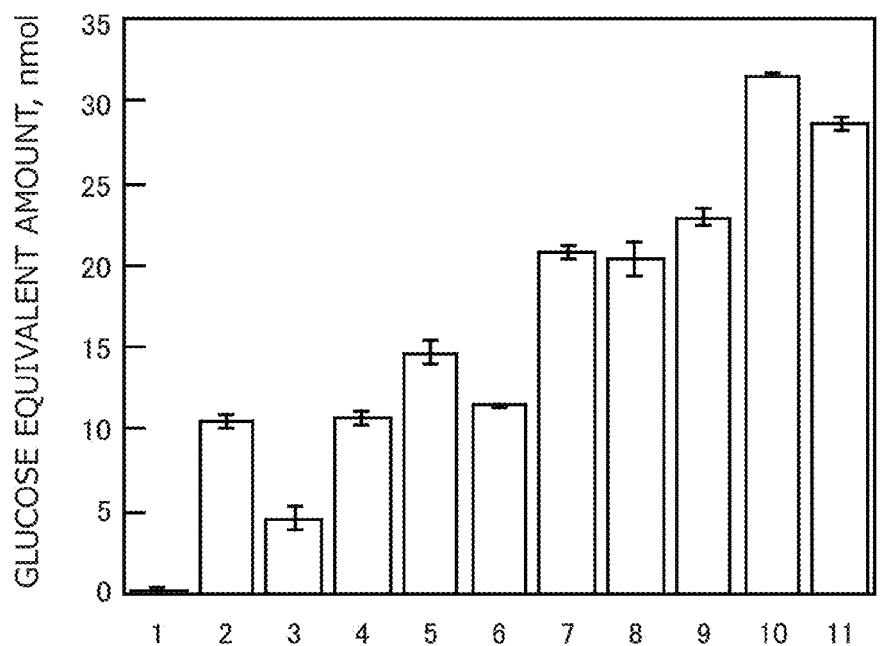

PARAMYLON DECOMPOSITION ACTIVITY OF
TRICHODERMA CELLULASE PREPARATION AND EgCel17A

1 : CELLULASE PREPARATION (2μg)
2 : CELLULASE PREPARATION (10μg)
3 : EgCel17A (0.4μg)
4 : EgCel17A (2μg)
5 : EgCel17A (4μg)
6 : CELLULASE PREPARATION (2μg) AND EgCel17A (0.4μg)
7 : CELLULASE PREPARATION (2μg) AND 2 mg EgCel17A
8 : CELLULASE PREPARATION (2μg) AND EgCel17A (4μg)
9 : CELLULASE PREPARATION (10μg) AND EgCel17A (0.4μg)
10 : CELLULASE PREPARATION (10μg) AND EgCel17A (2μg)
11 : CELLULASE PREPARATION (2μg) AND EgCel17A (4μg)

FIG. 17
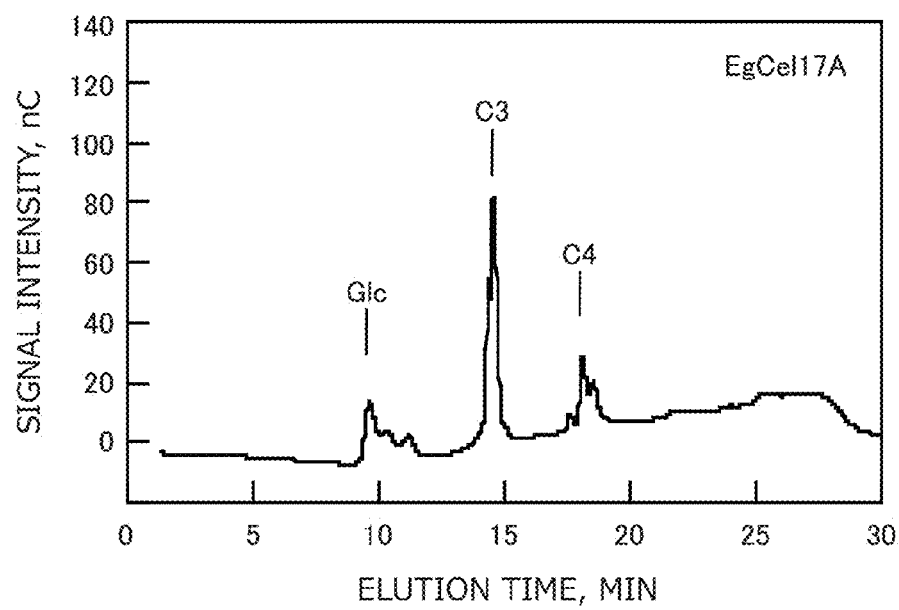
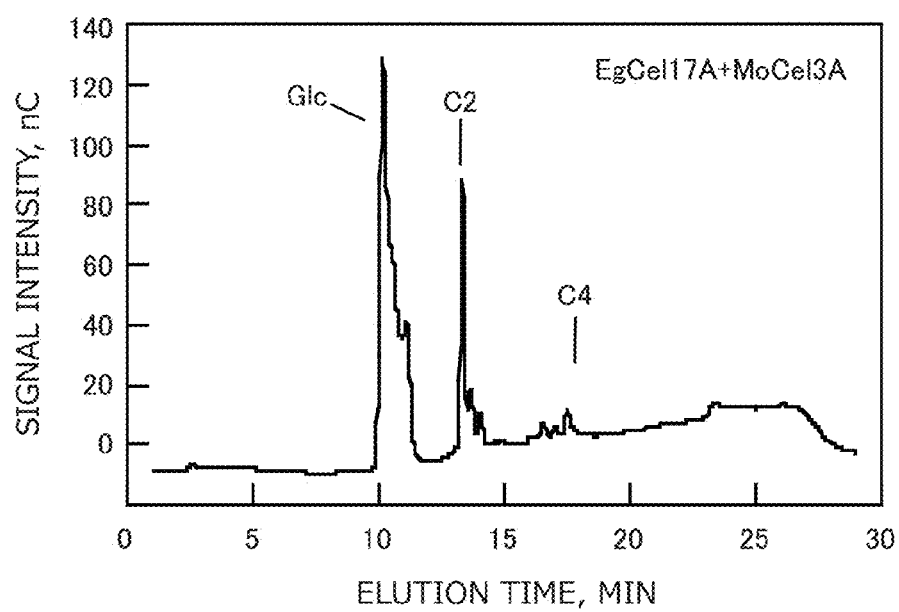

Glc : GLUCOSE
L2~L7 : LAMINARIOLIGOSACCHARIDE
HAVING POLYMERIZATION DEGREE
OF 2 TO 7

1 : AFTER 0 HOUR REACTION
2 : AFTER 0.5 HOUR REACTION
3 : AFTER 1 HOUR REACTION
4 : AFTER 2 HOUR REACTION
5 : AFTER 4 HOUR REACTION
6 : AFTER 18 HOUR REACTION

US 9,644,193 B2

β-1,3-GLUCANASE, POLYNUCLEOTIDE, RECOMBINANT VECTOR, TRANSFORMANT, PRODUCTION METHOD FOR β-1,3- GLUCANASE, ENZYME PREPARATION, AND PRODUCTION METHOD FOR PARAMYLON HAVING REDUCED MOLECULAR WEIGHT

CROSS REFERENCE TO RELATED APPLICATIONS

This application is a National Stage of International Application No. PCT/JP2014/070459 filed Aug. 4, 2014, claiming priority based on Japanese Patent Application Nos. 2013-161588 filed Aug. 2, 2013 and 2013-184351 filed Sep. 5, 2013, the contents of all of which are incorporated herein by reference in their entirety.

TECHNICAL FIELD

The present invention relates to a novel β-1,3-glucanase that decomposes paramylon, a polynucleotide, a recombinant vector, a transformant, a method for producing a β-1,3-glucanase, an enzyme preparation, and a method for producing low-molecular-weight paramylon.

BACKGROUND ART

A β-1,3-glucan is a polysaccharide having a β-1,3-bond of glucose as a main chain, and is present as a main structure in laminaran that is contained much in brown algae and the genus *Laminaria*, and in curdlan that is produced extracellularly by mutant strains of soil bacteria (*Alcaligenes faecalis*). Further, callose contained in cell walls of grains is also known.

β-1,3-glucans have a common characteristic of having a β-1,3-structure as a main chain, but depending on the origins thereof and the like, they are different from one another in terms of the presence/absence and the position of a branched side chain, the combination with a β-1,4-bond and a β-1,6-bond, the molecule size, and the like, thereby having different structures and properties, respectively.

A β-1,3-glucanase is an enzyme that hydrolyzes these β-1,3-glucans, and is used as an additive for fodders for improving body weight gains and feed demand ratios of domestic animals, as a physical property improving agent or a texture improving agent for confectionery, bread, and the like, and as an extraction efficiency improving agent for extracting yeast extract, and beer filtering efficiency improving agent, as well as for other various purposes.

There are β-1,3-glucanases that are derived from various origins, and have various substrate specificities, among which those exhibiting decomposition activity with respect to laminaran, curdlan, yeast cell walls, mycelium of *lentinus edodes*, pastoran, and the like, are known (Patent Documents 1 to 3).

CITATION LIST

Patent Document

PATENT DOCUMENT 1: JP 2005-34146A
PATENT DOCUMENT 2: JP 2005-224230A
PATENT DOCUMENT 3: JP H10(1998)-507078A

No decomposition enzyme has been known that would exhibit decomposition activity with respect to paramylon derived from the genus *Euglena*, paramylon being one type of β-1,3-glucan.

Among the β-glucans, paramylon has a characteristic of being composed of only β-1,3-bonds. Further, paramylon exists in a granular form in *euglena* cells of all of species and varieties, and the number, the shape, and the uniformity of particles of paramylon are characterized depending on the species. As is the case with the other β-glucans, paramylon is expected to have functionality, but much remains unknown regarding the mechanism of action thereof.

Besides, neither any decomposition enzyme that decomposes paramylon nor any composition resulting from decomposition of paramylon is known.

Incidentally, an attempt to reinforce an energy-supply system that utilizes biomass and the like, which is a local unutilized resource, as inexhaustible resources that can substitute for exhaustible resources such as petroleum, has been promoted.

Biomass is defined as reproducible organic resources derived from living organisms, except for fossil resources. Biomass refers to resources that are synthesized by living organisms using solar energy, that are inexhaustible as long as life and the sun exist, and that do not increase carbon dioxide in the atmosphere even if burnt or the like, that is, that are carbon neutral resources.

Bioethanol is being developed as one of energies utilizing biomass. Bioethanol is produced by performing ethanol fermentation, distillation, and dehydration with respect to the following: saccharide of sugarcane, corn, or the like; a substance obtained by saccharifying, with enzyme, a starch-based raw material such as rice, wheat, corn, or the like; or a substance obtained by pretreating a cellulosic raw material such as thinnings, construction waste materials, rice straw, bagasse, or the like with pressurized hot water, acid, or alkali and saccharifying the same with a saccharification enzyme or the like (the Ministry of Agriculture, Forestry and Fisheries, *the Biomass Industrialization Strategy* (Sep. 6, 2012), Reference Materials: Summary of the Principal Techniques).

Fossil fuel such as petroleum and the like is abundant in reserves, and has been stably supplied globally. In contrast, regarding bioethanol, it is difficult to ensure the supply amount sufficient for supplying the same globally or over an entire country in the present circumstances, since waste materials or the like are used as raw materials in many cases in response to requests with view to sustainability, considering that such raw materials do not conflict with food and do not cause such a situation where arable lands for raw materials encroach arable lands for foods. Generally, therefore, attempts for energy supply utilizing biomass or the like are promoted in individual regions.

Bioethanol has been applied to practical use in a part of regions, but as compared with fossil fuel such as petroleum and the like, bioethanol has weaker price competitiveness, and has problems regarding stable supply and sustainability. In Japan, therefore, bioethanol has not yet been in sufficiently widespread use. Development of raw materials for bioethanol having practicability in terms of costs, stable supply, and sustainability is desired.

On the other hand, mass culture of *euglena* was considered difficult in the past, but in recent years, as a result of earnest studies by the inventors of the present invention, techniques for mass culture of the same have been established, and the way for supplying paramylon in large quantities has been opened. This leads to a desire for the development of functional substances derived from *euglena*, which now can be supplied in large quantities.

SUMMARY OF INVENTION

Technical Problem

The present invention was made in light of the above-described problems, and an object of the present invention is to provide a β-1,3-glucanase that exhibits decomposition activity of decomposing paramylon derived from the genus *Euglena*.

Another object of the present invention is to provide a β-1,3-glucanase that is usable as a paramylon decomposition enzyme that converts paramylon derived from the genus *Euglena* into a raw material for bioethanol.

Still another object of the present invention is to develop a new functional substance derived from *euglena*, which now can be supplied in large quantities.

Solution to Problem

The inventors of the present invention, as a result of earnest studies, found that a novel β-1,3-glucanase having paramylon decomposition activity can be obtained from the genus *Euglena*, and arrived to the present invention.

As described above, mass culture of *euglena*, which accumulates paramylon, was considered difficult in the past, but in recent years, with earnest studies by the inventors of the present invention, techniques for mass culture of the same were established, and the way for supplying paramylon in large quantities was opened. Further, mass production of paramylon can be performed in a culture vessel of *euglena*, and does not require extended farm lands, unlike sugarcane, corn, and the like. Still further, since currently *euglena* is not food, there is no problem in terms of sustainability. Besides, since *euglena* has superior production efficiency, it is expected that supply stability can be ensured, which causes *euglena* to be considered as an expected candidate for a raw material of bioethanol.

Further, since paramylis is a linear polysaccharide composed of β-1,3-bonds alone, the saccharifying step can be simplified, as compared with cellulosic raw materials.

The above-described problems are solved by a β-1,3-glucanase that is derived from the genus *Euglena* and exhibits properties indicated below:
  (1) Effect: hydrolyzing a β-1,3-bond of a β-1,3-glucan.

The β-1,3-glucanase may be a β-1,3-glucanase that additionally exhibits properties indicated below:
  (2) substrate specificity: decomposing at least paramylon;
  (3) decomposition activity: the ratio of paramylon decomposition activity with respect to laminarin decomposition activity is 20% or higher;
  (4) optimum pH: 3.7 to 7.0;
  (5) optimum temperature: 30° C. to 70° C.; and
  (6) decomposition activity: the ratio of paramylon decomposition activity with respect to alkali-swollen paramylon decomposition activity is 25% or higher.

The studies by the inventors of the present invention in recent years enabled to find a novel β-1,3-glucanase derived from *euglena*, which now can be supplied in large quantities, thereby opening the way for novel utilization of *euglena*. It is known that properties of β-glucanase such as substrate specificity and the like vary with the origin thereof, and the finding of a β-1, 3-glucanase derived from *euglena* opens the way for providing a novel low-molecular-weight glucan and a method for producing the same, and further, opened the way for supplying a novel bioethanol raw material in which a novel low-molecular-weight glucan is used.

The β-1,3-glucanase may have a substrate specificity of decomposing alkali-swollen paramylon and laminarin, in addition to the substrate specificity of decomposing paramylon. Besides, the optimum temperature during a reaction time up to one hour may be 50° C. or higher, the optimum temperature during a reaction time from one hour up to two hours may be 40° C. or higher, and the optimum temperature during a reaction time of 20 hours or more may be 60° C. or lower.

Further, the above-described problems are solved by a β-1,3-glucanase made up of an amino acid sequence (a) or (b) shown below:
  (a) an amino acid sequence set forth in SEQ ID NO. 2, 4, or 6; and
  (b) an amino acid sequence that is obtained by deleting, substituting, or adding one or several amino acids with respect to an amino acid sequence set forth in SEQ ID NO. 2, 4, or 6, and that has hydrolysis activity of hydrolyzing a β-1,3-bond of a β-1,3-glucan.

Further, the above-described problems are solved by a polynucleotide made up of a base sequence (a) or (b) shown below:
  (a) a base sequence set forth in SEQ ID NO. 1, 3 or 5; and
  (b) a base sequence that is obtained by deleting, substituting, or adding one or several bases with respect to abase sequence set forth in SEQ ID NO. 1, 3 or 5, and that encodes a protein having hydrolysis activity of hydrolyzing a β-1,3-bond of a β-1,3-glucan.

Here, a recombinant vector including the above-described polynucleotide may be provided.

Further, a transformant including the above-described recombinant vector may be provided.

Further, there may be provided a method for producing a β-1,3-glucanase, the method including culturing the above-described transformant in a culture medium, generating and storing the β-1,3-glucanase in the culture product, and collecting the β-1,3-glucanase from the culture product.

An enzyme preparation for reducing the molecular weight of paramylon, containing the above-described β-1,3-glucanase, may be provided.

A method for producing low-molecular-weight paramylon, the method including allowing the β-1,3-glucanase to act on paramylon, to generate low-molecular-weight paramylon, may be provided.

Here, a glucosidase, together with the β-1,3-glucanase, may be allowed to act on the paramylon, so that glucose is generated as a main product generated from the low-molecular-weight paramylon.

Advantageous Effects of Invention

According to the present invention, by hydrolyzing paramylon, a novel low-molecular-weight paramylon can be obtained that is composed of straight-chain oligosaccharides and that has functionality.

Further, the present invention enables to hydrolyze a β-1,3-glucan containing paramylon. By utilizing the method for producing low-molecular-weight paramylon according to the present invention as a saccharifying step for bioethanol, a β-1,3-glucan such as paramylon or the like can be used as a raw material for bioethanol.

BRIEF DESCRIPTION OF DRAWINGS

FIG. 10 is a graph showing paramylon decomposition activity by *Trichoderma* cellulase preparation and the enzyme EgCel17A, which is an example of the present invention.

FIG. 17 is a graph showing results of HPLC of reaction products obtained by adding EgCel17A, and MoCel3A to alkali-swollen paramylon to cause reactions.

DESCRIPTION OF EMBODIMENTS

Figure 1:
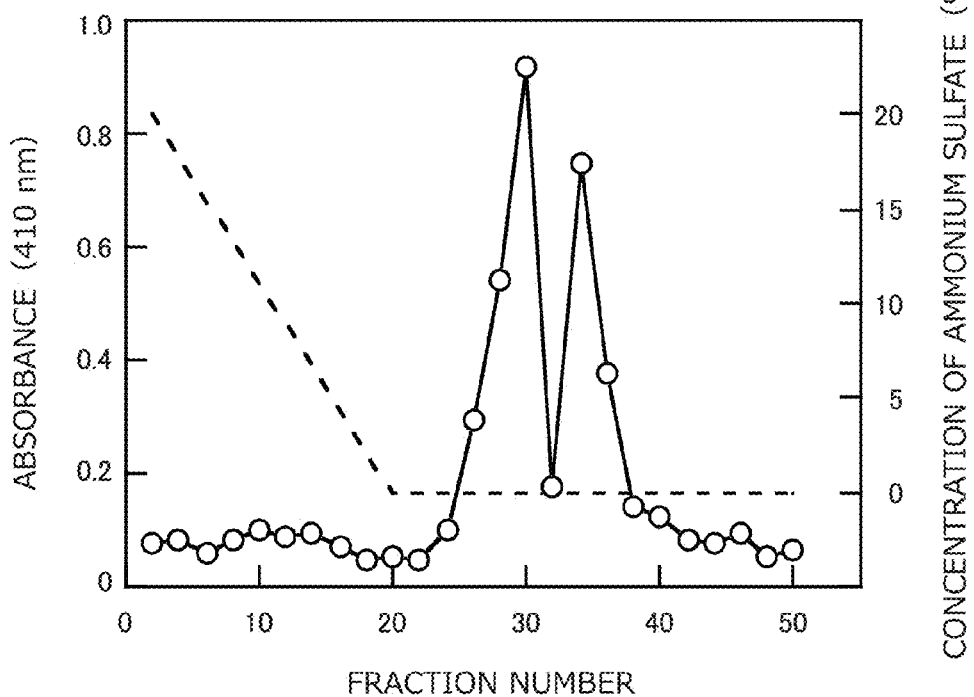
FIG. 1 is a graph showing separation of laminarin decomposition activity fractions of a solution of disrupted *euglena* by a hydrophobic column.

Hereinafter the present invention is described in detail.
The present invention relates to a β-1,3-glucanase derived from the genus *Euglena*.

In the β-1,3-glucanase of the present invention, a protein having decomposition activity of decomposing paramylon produced by the genus *Euglena* is contained.

Paramylon is a macromolecule β-1,3-glucan) in which about 700 glucoses are polymerized with β-1,3-bonds, and is a storage polysaccharide that the genus *Euglena* contains. Paramylon particles are particles each of which is in a flat spheroidal shape and is formed with β-1,3-glucan chains spirally twining.

The paramylon particles are isolated from genus *Euglena* cultured, and purified into a microparticle form, by arbitrary appropriate methods, and are provided in a powder form usually.

For example, the paramylon particles can be obtained by the following: (1) culturing *euglena* cells in an arbitrary appropriate culture medium; (2) separating the *euglena* cells from the culture medium; (3) isolating paramylon from the separated *euglena* cells; (4) purifying the paramylon thus isolated; and, optionally, (5) cooling the same, and thereafter freeze-drying the same. As the *euglena* cells, all types of *euglena* cells can be used, for example, *Euglena gracilis*, *Euglena intermedia*, and *Euglena piride*, as well as other *euglena* types, for example, *Astaia longa*, can be used.

The culture of *euglena* cells can be performed by, for example, the supply batch method. The separation of *euglena* cells can be performed by, for example, centrifugation or simple sedimentation of culture solution. The isolation of paramylon can be performed by, for example, using a nonionic or anionic surfactant of a mostly biodegradable type. The purification of paramylon can be performed substantially simultaneously with the isolation.

More specifically, for example, the following procedure can be taken: *Euglena gracilis* powder (produced by Euglena Co., Ltd.) is put in distilled water, and is agitated at room temperature for two days. This is subjected to an ultrasonic treatment so that cell films are destroyed, and coarse paramylon particles are collected by centrifugation. The collected paramylon particles are dispersed in 1% aqueous solution of sodium dodecyl sulfate, are treated at 95° C. for two hours. The paramylon particles, collected by centrifugation again, are dispersed in 0.1% aqueous solution of sodium dodecyl sulfate, and are treated at 50° C. for 30 minutes. Lipids and proteins are removed by this operation, and thereafter, the particles are washed with acetone and ether and dried at 50° C., whereby purified paramylon particles can be obtained. The isolation and purification of paramylon from *euglena* is known, which is disclosed in, for example, E. Ziegler, "Die naturlichen and kunstlichen Aromen" Heidelberg, Germany, 1982, Chapter 4.3 "Gefriertrocken", DE 43 28 329, and JP2003-529538A.

Examples of β-1,3-glucanase include β-1,3-glucanase derived from *Euglena gracilis* (*E. gracilis*), particularly, β-1,3-glucanase derived from *Euglena gracilis* (*E. gracilis*) Z strain.

Besides the above-described ones, the β-1,3-glucanase may be the following species: *Euglena gracilis*; *Euglena gracilis* Klebs; and *Euglena gracilis* var. *bacillaris*. Alternatively, the β-1,3-glucanase may be a SM-ZK strain as a mutant strain of *Euglena gracilis* (*E. gracilis*) Z strain (chloroplast-lacking strain), var. *bacillaris* as a variety thereof, β-1,3-glucanase derived from a gene mutation strain, such as chloroplast mutant strains of these species, etc.

The genus *Euglena* is widely distributed in fresh water in ponds and marshes, and *Euglena* separated from these may be used, or alternatively, arbitrary one of *Euglena* that is already isolated may be used.

The genus *Euglena* of the present invention encompasses all of the mutant strains. Further, those obtained by genetic approaches, for example, recombination, transduction, transformation, and the like are included in these mutant strains.

Further, other examples of β-1,3-glucanase of the present invention include a protein made up of an amino acid sequence set forth in SEQ ID NOS. 2, 4, or 6 in the sequence listing.

Figure 4:
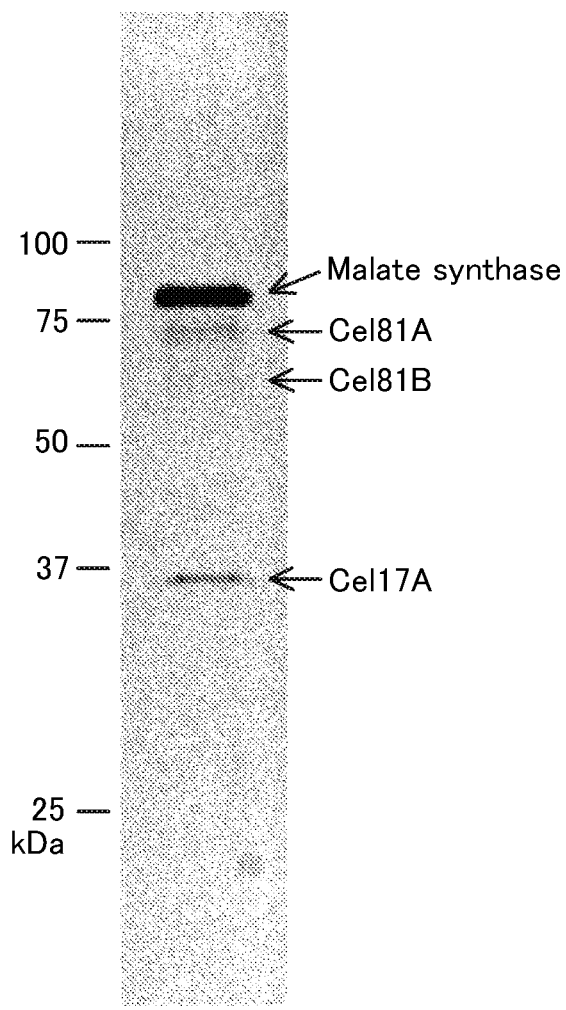
FIG. 4 illustrates SDS-PAGE gel silver staining showing laminarin decomposition activity fractions of a solution of disrupted *euglena*.

The amino acid sequence set forth in SEQ ID NO. 2 is named as "EgCel17A" in the present description, which was detected as the lowest band in a fluorescence imaging of a gel subjected to the sodium dodecyl sulfate-polyacrylamide gel electrophoresis (SDS-PAGE) in Example 2, which is illustrated in FIG. 4. A nucleotide sequence including a gene that encodes the protein made up of the amino acid sequence set forth in SEQ ID NO. 2 is set forth in SEQ ID NO. 1.

The amino acid sequence set forth in SEQ ID NO. 4 is named as "EgCel81A" in the present description, which was detected as the second lowest band in the fluorescence imaging of a gel subjected to SDS-PAGE in Example 2, which is illustrated in FIG. 4. A nucleotide sequence including a gene that encodes the protein made up of the amino acid sequence set forth in SEQ ID NO. 4 is set forth in SEQ ID NO. 3.

The amino acid sequence set forth in SEQ ID NO. 6 is named as "EgCel81B" in the present description, which was detected as the third lowest band in the fluorescence imaging of a gel subjected to SDS-PAGE in Example 2, which is illustrated in FIG. 4. A nucleotide sequence including a gene that encodes the protein made up of the amino acid sequence set forth in SEQ ID NO. 6 is set forth in SEQ ID NO. 5.

Further, a protein that is obtained by substituting, deleting, inserting, and/or adding one or several amino acid residues with respect to one or several sites in a protein made up of the amino acid sequence set forth in SEQ ID NOS. 2, 4, or 6 is also encompassed by the present invention, as long as the protein has glyceroglycolipid decomposition activity. The term "several" signifies the numerical value of not more than 75, and preferably refers to the numerical value of not more than 50, further preferably the numerical value of not more than 25, and still further preferably the numerical value of not more than 10.

As another example of the protein, a protein having nucleotide sequence homology, identity or similarity of 70% or more, more preferably 80% or more, further preferably 90% or more, or particularly preferably 95% or more with respect to the protein made up of the amino acid sequence set forth in SEQ ID NOS. 2, 4, or 6, is encompassed by the present invention, as long as the protein has glyceroglycolipid decomposition activity.

The phrase "polynucleotide of the present invention" refers to a polynucleotide that encodes the β-1,3-glucanase of the present invention. The polynucleotide may have any morphology that is known presently, such as cDNA, genome DNA, artificially modified DNA, or chemically synthesized DNA.

Examples of a polynucleotide of the present invention include a DNA that has a nucleotide sequence set forth in nucleotide Nos. 1 to 1,611 in SEQ ID NO. 1, and that encodes a protein having paramylon decomposition activity; a DNA that has a nucleotide sequence set forth in nucleotide Nos. 1 to 3,119 in SEQ ID NO. 3, and that encodes a protein having paramylon decomposition activity; and a DNA that has a nucleotide sequence set forth in nucleotide Nos. 1 to 2,756 in SEQ ID NO. 5, and that encodes a protein having paramylon decomposition activity.

Other examples of the polynucleotide of the present invention include a DNA that has nucleotide sequence homology, identity or similarity of 70% or more, more preferably 80% or more, further preferably 90% or more, or particularly preferably 95% or more with respect to the nucleotide sequence set forth in nucleotide Nos. 1 to 1,611 in SEQ ID NO. 1, the nucleotide sequence set forth in nucleotide Nos. 1 to 3,119 in SEQ ID NO. 3, or the nucleotide sequence set forth in nucleotide Nos. 1 to 2,756 in SEQ ID NO. 5, and that encodes a protein having paramylon decomposition activity. Examples of such a DNA include variant DNAs discovered in the natural world, artificially modified variant DNAs, homologous DNAs derived from different species of organisms, identical DNAs, or similar DNAs.

Other examples of the polynucleotide of the present invention include DNAs that respectively hybridize under stringent conditions with the nucleotide sequence set forth in nucleotide Nos. 1 to 1,611 in SEQ ID NO. 1, the nucleotide sequence set forth in nucleotide Nos. 1 to 3,119 in SEQ ID NO. 3, and the nucleotide sequence set forth in nucleotide Nos. 1 to 2,756 in SEQ ID NO. 5, and that encodes a protein that has paramylon decomposition activity.

Further, a polynucleotide including a polynucleotide made up of the nucleotide sequence set forth in nucleotide Nos. 1 to 1,611 in SEQ ID NO. 1, the nucleotide sequence set forth in nucleotide Nos. 1 to 3,119 in SEQ ID NO. 3, or the nucleotide sequence set forth in nucleotide Nos. 1 to 2,756 in SEQ ID NO. 5 is also encompassed by the present invention, as long as the polynucleotide includes a region for encoding a protein having paramylon decomposition activity.

Further, examples of the β-1,3-glucanase of the present invention include proteins made up of amino acid sequences encoded by the polynucleotides of the present invention.

Further, examples of the β-1,3-glucanase of the present invention include modifications produced by modifying the polynucleotide of the present invention by a known method of shortening a DNA from an end thereof or by cassette mutation so that one or more arbitrary amino acids are deleted therefrom.

In this way, even a protein obtained based on the polynucleotide of the present invention by genetic engineering techniques is encompassed by the present invention as long as the protein has paramylon decomposition activity.

Such a β-1,3-glucanase does not necessarily have an entirety of the amino acid sequence set forth in SEQ ID NOS. 2, 4, or 6, but even a protein made up of, for example, a part of the sequence is encompassed by the β-1,3-glucanase of the present invention as long as the protein has paramylon decomposition activity. Further, a DNA encoding such a β-1,3-glucanase is also encompassed by the present invention.

As the culture solution for culturing the genus *Euglena*, for example, a culture solution to which nutrient salts such as a nitrogen source, a phosphorus source, minerals, and the like are added, can be used, which is, for example, a modified Cramer-Myers medium (($NH_4$)$_2HPO_4$: 1.0 g/L, $KH_2PO_4$: 1.0 g/L, $MgSO_4·7H_2O$: 0.2 g/L, $CaCl_2·2H_2O$: 0.02 g/L, $Fe_2(SO_2)_3·7H_2O$: 3 mg/L, $MnCl_2·4H_2O$: 1.8 mg/L, $CoSO_4·7H_2O$: 1.5 mg/L, $ZnSO_4·7H_2O$: 0.4 mg/L, $Na_2MoO_4·2H_2O$: 0.2 mg/L, $CuSO_4·5H_2O$: 0.02 g/L, thiamine hydrochloride (vitamin $B_1$): 0.1 mg/L, cyanocobalamin (vitamin $B_{12}$), (pH3.5)). ($NH_4$)$_2HPO_4$ may be replaced with ($NH_4$)$_2SO_4$ or $NH_3$aq. Further, other than the above-described ones, a known Hutner medium, or a known Koren-Hutner medium, prepared according to the descriptions in "*Euglena* physiology and biochemistry" edited by Shozaburo Kitaoka, Gakkai Shuppan Center, may be used.

The culture solution has pH of preferably 2 or more, and the upper limit of the pH is preferably 6 or less, and more preferably 4.5 or less. By setting pH on the acidic side, photosynthetic microorganisms are allowed to predominantly grow as compared with the other microorganisms, whereby contamination can be suppressed.

The culture temperature, the pH, and the aeration and agitation rate, however, can be appropriately selected to be suitable for the production of β-1,3-glucanase using *euglena*.

Further, the culture of the genus *Euglena* may be performed by any liquid culture method such as flask culture, culture using a fermenter, the batch culture method, the semi-batch culture method (the fed-batch culture method), or the continuous culture method (the perfusion culture method).

The β-1,3-glucanase of the present invention may be a β-1,3-glucanase obtained by purifying or partially purifying disruption liquid of the genus *Euglena* disrupted.

A β-1, 3-glucanase also may be used, which is obtained by, after the culture of the genus *Euglena* is finished, obtaining a disruption solution containing the genus *Euglena* disrupted, and partially purifying, or purifying this disruption solution by subjecting the same to a normal reconstruction treatment, a treatment with a protein precipitant (the salting-out method), centrifugation, the osmotic shock method, the freeze-thaw method, ultrasonic disruption, ultrafiltration, gel filtration, any of various types of liquid chromatography such as adsorption chromatography, ion-exchange chromatography, affinity chromatography, and high-performance liquid chromatography (HPLC), the dialysis method, or a combination of these.

Further, the β-1,3-glucanase of the present invention can be obtained also by the following process: a host cell is transformed with a recombinant plasmid obtained by inserting the DNA of the present invention into a plasmid vector, and the β-1,3-glucanase is obtained from a culture product of this transformed cell. Such a recombinant plasmid obtained by inserting a DNA of the present invention into an appropriate vector is also encompassed by the present invention.

As the vector, a plasmid vector is suitably used, but various types of known vectors such as a cosmid vector, a bacteriophage, a virus vector, an artificial chromosome vector, and the like can be used.

With such a vector, host cells of other prokaryotes, or eukaryotes can be transformed. Further, by using a vector having an appropriate promoter sequence and/or a sequence relating to phenotypic expression, or alternatively by transfecting such a sequence to make the same an expression vector, a gene can be caused to express in each host.

By transfecting the vector into a host cell, the cell can be obtained. The host cell may be a prokaryotic cell or a eukaryotic cell as long as it is a cell in which the vector can be transfected.

As a host cell that is a prokaryotic cell, for example, koji mold (*Aspergillus oryzae*) can be suitably used, but other than the same, *Escherichia coli, Bacillus subtilis*, or the like also can be used.

Further, as koji mold, other than *Aspergillus oryzae*, the following types of koji mold belonging to the genus *Aspergillus* can be used: *Aspergillus sojae*; *Aspergillus awamori*; *Aspergillus kawachii*; *Aspergillus usami*; *Aspergillus tamari*; and *Aspergillus Glaucus*.

As a host cell that is an eukaryotic cell, for example, cells of vertebrate animals, insects, and yeasts can be used.

In a case where *Aspergillus oryzae* (*A. oryzae*) is used as a host cell, it is preferable to use, as a plasmid vector, an *Aspergillus oryzae* expression vector pPPamyBSP utilizing an α-amylase gene promoter (amyBp).

The gene transfection to a cell can be suitably performed by preparing a protoplast of an *Aspergillus oryzae* host, and using a known protoplast PEG method (the polyethylene glycol method), but the same can be performed also by another known transfection technique such as the lipofection method, the electroporation method, the nucleofection method, the calcium phosphate method, the injection method, the microinjection method, or the like.

The transformant of the present invention, which is obtained by transfecting a vector into a host cell, can be cultured in the usual way, and by culturing the same, the β-1,3-glucanase of the present invention is intracellularly or extracellularly produced.

As a culture medium used for culturing the transformant, any can be appropriately selected from various types of commonly used media, depending on the host cell used.

In a case where *Aspergillus oryzae* is used as a host cell, a known culture medium such as YPM medium can be used. Further, other than this, a potato dextrose agar (PDA) medium, a potato dextrose broth (PDB) medium, a bran medium containing wheat bran, or the like may be used.

The β-1,3-glucanase of the present invention, which is produced as a recombinant protein inside or outside the cells of a transformant by culturing the transformant, can be separated and purified from a culture product by any of various types of separation operations utilizing physico-chemical properties, chemical properties, biochemical properties (enzyme activity, etc.), and the like of the protein. For example, the following can be used: a normal reconstruction treatment; a treatment with a protein precipitant (the salting-out method); centrifugation; the osmotic shock method; the freeze-thaw method; ultrasonic disruption; ultrafiltration; gel filtration; any of various types of liquid chromatography such as adsorption chromatography, ion-exchange chromatography, affinity chromatography, and high-performance liquid chromatography (HPLC); the dialysis method; and combinations of these.

For example, in a case where the β-1,3-glucanase of the present invention, which is produced as a recombinant protein, is secreted to outside cells, distilled water is added to the culture medium and the culture medium is agitated, left to stand at room temperature for about three hours, and thereafter is filtered by filter paper, whereby the β-1,3-glucanase of the present invention can be extracted.

Further, in a case where the β-1,3-glucanase of the present invention produced as a recombinant protein is locally present inside cells, for example, a buffer solution is added to the culture medium, and the medium is disrupted using a disruption device driven intermittently while being iced, and the disruption liquid obtained is centrifuged so that supernatant is collected, whereby the β-1,3-glucanase of the present invention can be extracted.

Thus, by culturing the transformant of the present invention and separating and purifying the culture product and so on, the β-1,3-glucanase of the present invention can be produced at a high yield on an industrial scale.

Specific properties of the β-1,3-glucanase obtained from a transformant into which the polynucleotide of the present invention is transfected are indicated below, though the properties that the β-1,3-glucanase of the present invention has are not limited to these:

(1) effect: hydrolyzing a β-1,3-bond of a β-1,3-glucan;
(2) substrate specificity: decomposing paramylon;
(3) decomposition activity: the ratio of paramylon decomposition activity with respect to laminarin decomposition activity is 20% or higher;
(4) optimum pH: the optimum pH is 3.7 to 7.0;
(5) optimum temperature: the optimum temperature during a reaction time up to one hour is 50° C. or higher, the optimum temperature during a reaction time from one hour up to two hours is 40° C. or higher, and the optimum temperature during a reaction time of 20 hours or more is 60° C. or lower; and
(6) decomposition activity: the ratio of paramylon decomposition activity with respect to alkali-swollen paramylon decomposition activity is 25% or higher.

Further, a method for producing low-molecular-weight paramylon wherein the β-1,3-glucanase is caused to act on paramylon so that low-molecular-weight paramylon is generated is also encompassed by the present invention.

In the method for producing low-molecular-weight paramylon according to the present invention, the β-1,3-glucanase derived from the genus *Euglena* according to the present invention is added to paramylon suspension liquid that is obtained by suspending paramylon powder in a buffer such as water or phosphate buffer, and is incubated at pH 3.7 to 7.0, at a temperature of 30 to 70° C., for 15 minutes to 20 hours, so that the β-1,3-glucanase is caused to act on paramylon.

With this, β-1,3-bonds of paramylon are hydrolyzed by the β-1,3-glucanase, whereby low-molecular-weight paramylon is generated.

Here, "low-molecular-weight paramylon" refers to a saccharide generated by hydrolysis of the β-1,3-bonds of paramylon, and encompasses glucose, and oligosaccharides having a polymerization degree of 2 or more in which two or more glucoses are linked by β-1,3-bonds.

Further, in the method for producing low-molecular-weight paramylon according to the present invention, MoCel3A as a glucosidase derived from *Magnaporthe oryzae*, together with the β-1,3-glucanase derived from the genus *Euglena* according to the present invention, may be added to the paramylon suspension liquid.

Still further, the enzyme to be added together with the β-1,3-glucanase is not limited to this, and the enzyme may be another glucanase or glucosidase.

Still further, in the place of paramylon powder, alkali-swollen paramylon may be used. In a case where alkali-swollen paramylon is used and an alkali treatment and neutralization are performed, the same may be added to a buffer after the salt concentration is reduced preliminarily.

EXAMPLES

Hereinafter, the present invention is described in more detail by way of examples. The present invention, however, is not limited to these.

Example 1

Preparation of β-1,3-Glucanase from *Euglena*

*Euglena gracilis* (*E. gracilis*) Z strain was suspended in a phosphate buffer (10 mM, pH 7.0), and thereafter, was disrupted by a sonicator, whereby a solution of disrupted *euglena* was obtained. The solution of disrupted *euglena* was centrifuged (22,000×g, 15 minutes), supernatant was collected therefrom, and ammonium sulfate (420 g/L) was added thereto.

This solution was left to stand at 4° C. for 30 minutes, and thereafter, centrifugation (22,000×g, 15 minutes) was performed, whereby precipitate was obtained.

The precipitate was dissolved with a phosphate buffer (10 mM, pH 7.0) containing 0.2 M ammonium sulfate, and was applied to a hydrophobic column (HiPrep phenyl, GE Healthcare) equilibrated with the same buffer.

The column was washed with a phosphate buffer containing 0.2 M ammonium sulfate (10 mM, pH 7.0), and thereafter, the concentration of ammonium sulfate was reduced, so that protein bound to the column was eluted.

In FIG. 1, the laminarin decomposition activity of each fraction herein is indicated by white circles, and the ammonium sulfate concentration upon elution is indicated by a dotted line. As illustrated in FIG. 1, fractions of fraction Nos. 26 to 36 exhibited high decomposition activity. These fractions of fraction Nos. 26 to 36 exhibiting high decomposition activity were collected.

Thereafter, the active fractions of fraction Nos. 26 to 36, which exhibited decomposition activity with respect to laminarin in the hydrophobic column, were applied to a gel filtering column (Superdex75, GE Healthcare) equilibrated with a phosphate buffer containing 0.2 M NaCl (10 mM, pH 7.0).

Figure 2:
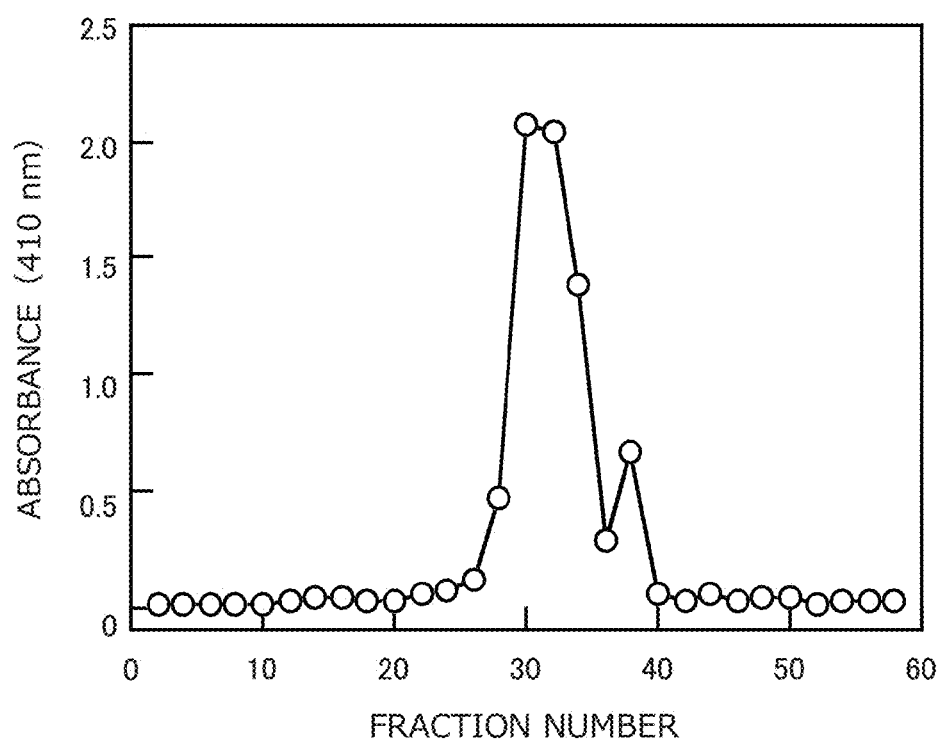
FIG. 2 is a graph showing separation of laminarin decomposition activity fractions of a solution of disrupted *euglena* by a gel filtration column.

As illustrated in FIG. 2, fractions of fraction Nos. 28 to 36 exhibited high laminarin decomposition activity. These fractions of fraction Nos. 28 to 36 exhibiting high decomposition activity were collected.

Thereafter, the active fractions of fraction Nos. 28 to 36, which exhibited decomposition activity with respect to laminarin in the gel filtering column, were applied to an anion-exchange column (MonoQ, GE Healthcare) equilibrated with a phosphate buffer (10 mM, pH 7.5). After the column was washed with a phosphate buffer (10 mM, pH 7.5), the concentration of NaCl was increased, so that proteins bound to the column were eluted.

Figure 3:
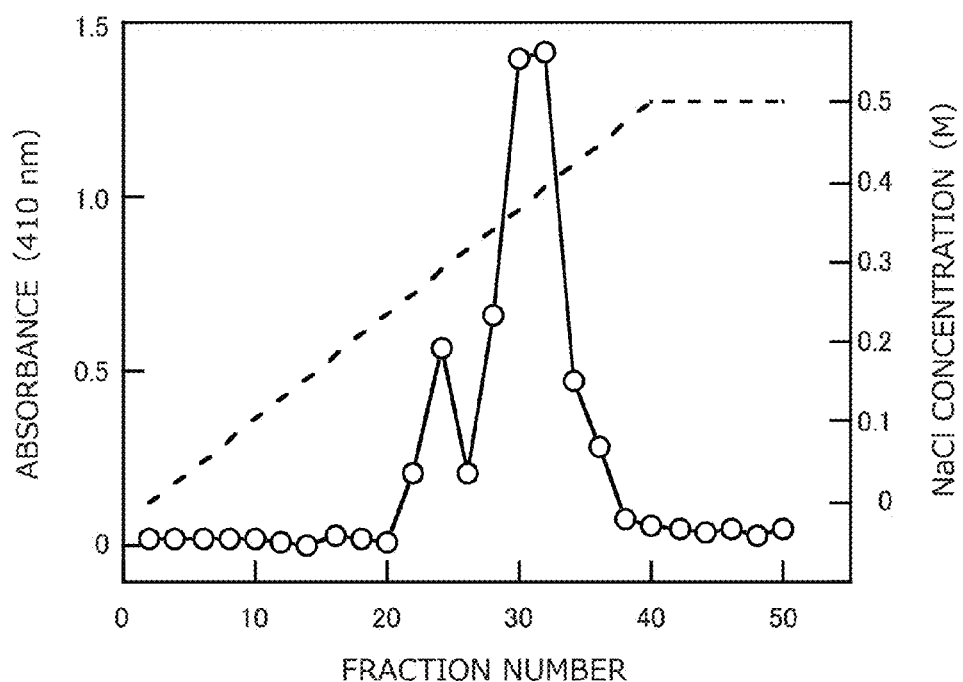
FIG. 3 is a graph showing separation of laminarin decomposition activity fractions of a solution of disrupted *euglena* by an anion-exchange column.

As illustrated in FIG. 3, fractions of fraction Nos. 28 to 34 exhibited high laminarin decomposition activity. These fractions of fraction Nos. 28 to 34, which exhibited high decomposition activity, were collected, whereby a partially purified β-1,3-glucanase was obtained.

Example 2

Determination of Amino Acid Sequence of β-1,3-Glucanase Derived from *Euglena*

The active fractions of fraction Nos. 26 to 36, having proteins partially purified and exhibiting decomposition activity with respect to laminarin in the ion replacing column in Example 1, were separated by sodium dodecyl sulfate-polyacrylamide gel electrophoresis (SDS-PAGE) with 12.5% gel, and were stained with Coomassie Brilliant Blue R-250 (CBB). FIG. 4 illustrates fluorescence imaging of gel obtained in electrophoresis. As illustrated in FIG. 4, four protein bands were detected.

Stained proteins were spliced out from the gel as gel pieces and digested with trypsin, whereby fragmented peptide mixture was obtained.

The fragmented peptide mixture having been treated with trypsin was separated and concentrated, using a hybrid-type mass analysis system (LTQ Orbitrap XL mass spectrometer; Thermo Fisher Scientific Inc.), according to the method suggested by Kawamura et al. (Kawamura, Y., and Uemura, M. (2003) *Mass spectrometric approach for identifying putative plasma membrane proteins of Arabidopsis leaves associated with cold acclimation*. Plant J. 36, 141-154), and mass analysis of fragmented peptide was performed at the same time, whereby a mass value of the peptide and MS/MS spectrum of fragmented ions were acquired. Thereafter, the amino acid sequence was analyzed by MASCOT MS/MS ion search (Matrix Science Inc.) by the sequence tag method.

Consequently, among the four bands illustrated in FIG. 4, the three proteins other than the malate synthase, which is the largest, were estimated to be enzymes responsible for polysaccharide decomposition.

Band 1 was named as "EgCel17A". Bands 2 and 3 were named as "EgCel81A" and "EgCel81B", respectively.

Amino acid sequences of EgCel17A, EgCel81A, and EgCel81B are shown in SEQ ID NOS. 2, 4, and 6, respectively.

Example 3

Identification of Polynucleotides Encoding β-1,3-Glucanases EgCel17A, EgCel81A, and EgCel81B Derived from *Euglena*

*Euglena gracilis* (*E. gracilis*) Z strain was cultured in a Koren-Hutner medium, 10 L, prepared according to the descriptions in *Euglena physiology and biochemistry* (edited by Shozaburo Kitaoka, Gakkai Shuppan Center), at 29° C. for 10 days. The medium was concentrated by centrifugation to about 6 times, and nitrogen gas was aerated through this medium until the dissolved oxygen concentration became 0.01 mg/L. This was hermetically sealed and was left to stand still for 24 hours, which were regarded anaerobically treated cells.

From *euglena* (100 mg) collected by centrifugation, total RNA was extract by using a RNA extraction kit (QIAGEN). From the total RNA thus prepared, with use of an oligo(dT) primer, a cDNA was synthesized by a reverse transcriptase (Transcriptase III, Invitrogen, Inc.). From partial gene sequences of EgCel17A, EgCel81A, and EgCel81B of the amino acid sequences of SEQ ID NOS. 2, 4, and 6 obtained in Example 2, the following were produced: as to EgCel17A, a 5'-Race primer and a 3'-Race primer set forth in SEQ ID NOS. 7 and 8, respectively; as to EgCel81A, a 5'-Race primer and a 3'-Race primer set forth in SEQ ID NOS. 9 and 10, respectively; as to EgCel81B, a 5'-Race primer and a 3'-Race primer set forth in SEQ ID NOS. 11 and 12, respectively.

Next, the gene sequence was read by the 5'-Race method and the 3'-Race method. GeneRacer (registered trademark) Kit (Invitrogen, Inc.) was used for synthesizing a cDNA. Further, using the DNA primers set forth in SEQ ID NOS. 7 to 12 and a DNA polymerase (GXL DNA polymerase, Takara Bio Inc.), PCR was performed.

All the gene sequences obtained were read by a DNA sequencer (Genome Analyzer IIx, Illumina, Inc.). The results of the gene sequence analysis are shown in SEQ ID NOS. 1, 3, and 5.

Example 4

Preparation of Recombinant Protein of EgCel17A i) Gene Transfection to EgCel17A

A secretion signal of nucleotide Nos. 72 to 152 was removed from the isolated EgCel17A gene set forth in SEQ ID NO. 1, and in accordance with the method suggested by Takahashi et al. (Takahashi M, Takahashi H, Nakano Y, Konishi T, Terauchi R, Takeda T (2010), *Characterization of a cellobiohydrolase (MoCel6A) produced from Magnaporthe oryzae*. Appl. Environ. Microbiol., 76, 6583-6590.), a histidine tag 5'-TTAGTGATGGTGATGGTGGTGATG-GCTAGG-3' (SEQ ID NO: 13), composed of seven consecutive histidines, was added to the 3'-terminal. This DNA was inserted to an *Aspergillus oryzae* expression vector pPPamyBSP using an α-amylase gene promoter (amyBp).

The plasmid DNA thus prepared was transfected into an *Aspergillus oryzae* strain RIB40 by the PEG method, and according to the method suggested by Takahashi et al., the gene-transfected strain was selected in a Czapek-Dox agar medium containing 0.1 mg/ml of pyrithiamine and 1% of glucose.

ii) Purification of Recombinant EgCel17A

The EgCel17A gene-transfected strain of *Aspergillus oryzae* obtained by selection at i) was inoculated in a YPM liquid medium (1% Yeast extract, 2% Peptone, 2% Maltose), and was subjected to shaking culture at 25° C., at 120 rpm, for two days. The gene-transfected strain of *Aspergillus oryzae* was removed by double-layer gauze, and then, the medium was concentrated by ultrafiltration. The solution obtained was applied to a histidine tag binding resin (Talon metal affinity resin, Clontech Laboratories, Inc.) equilibrated with a buffer solution (50 mM phosphate buffer (pH 7.0), 50 mM NaCl), and thereafter, the resin was washed with the same buffer solution.

Further, the resin was washed with 0.2× elution liquid (50 mM phosphate buffer (pH 7.0), 50 mM NaCl, 40 mM imidazole). Proteins bound to the resin were eluted by 1× elution liquid (50 mM phosphate buffer (pH 7.0), 50 mM NaCl, 40 mM imidazole), and the replacement with phosphate buffer (10 mM, pH 7.0) and concentration was performed by ultrafiltration. Through the above-described process, recombinant EgCel17A using *Aspergillus oryzae* as the host was obtained.

Figure 5:
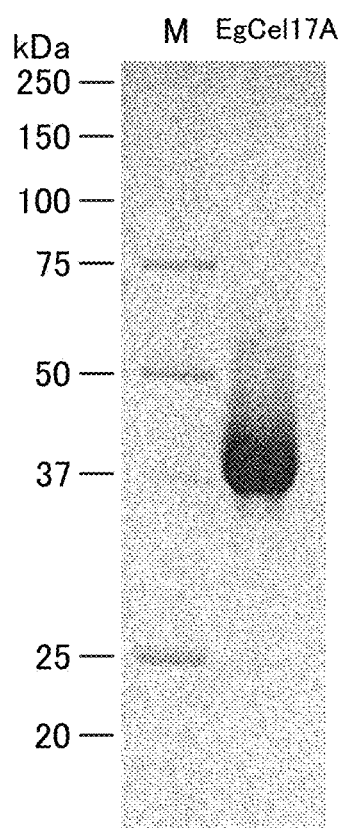
FIG. 5 illustrates a CBB stained image of SDS-PAGE gel of recombinant EgCel17A.

Recombinant EgCel17A (5 μg) produced using *Aspergillus oryzae* as the host was separated by SDS-PAGE, by the same method as that in Example 2, and thereafter, CBB staining was performed. FIG. 5 illustrates the results of the electrophoresis. As illustrated in FIG. 5, a band was detected at a position similar to that of EgCel17A obtained in Example 2.

Test Example 1

Properties of β-1, 3-Glucanase Derived from the Genus *Euglena* i) Substrate Specificity

Using the recombinant EgCel17A (0.2 μg) obtained in Example 4, decomposition activity with respect to a plurality of polysaccharides was examined, so that substrate specificity of EgCel17A was studied.

First, alkali-swollen paramylon was prepared. Paramylon powder (availed from Euglena Co., Ltd.) was suspended in water, NaOH solution was added thereto, and the solution obtained was shaken for 15 minutes at room temperature. Thereafter, the solution was neutralized with acetic acid, whereby alkali-swollen paramylon was obtained. This alkali-swollen paramylon was washed with water.

Next, a substrate, a phosphate buffer (100 mM, pH5.5), and an enzyme preparation (enzyme reaction solution, 50 μl, containing column elution liquid or 0.2 µg recombinant EgCel17A) were mixed, whereby a reaction solution was prepared.

Here, as a substrate, the following were used: 1,3-1,4-β-glucan derived from barley (availed from Megazyme Inc.); xyloglucan (availed from Megazyme Inc.); carboxymethyl cellulose (availed from Sigma-Aldrich Co., LLC); hydroxyethyl cellulose (availed from Sigma-Aldrich Co., LLC); xylan (availed from Sigma-Aldrich Co., LLC); laminarin (availed from Sigma-Aldrich Co., LLC); cellulose derived from cotton (availed from Sigma-Aldrich Co., LLC); phosphate-swellable cellulose (produced from cellulose by the inventors of the present invention); paramylon (availed from Euglena Co., Ltd.); and alkali-swollen paramylon.

The substrate concentration in the reaction solution was set to be 0.1% in the case where the substrate was 1,3-1,4-β-glucan, xyloglucan, carboxymethyl cellulose, hydroxyethyl cellulose, xylan, or laminarin, or cellulose, and was set to 1% in the case where the substrate was phosphate-swellable cellulose, paramylon, or alkali-swollen paramylon.

In this way, phosphate-swellable cellulose, paramylon, and alkali-swollen paramylon, which are water-insoluble substrates, were added more to the reaction system, as compared with the water-soluble substrate.

The prepared reaction solution was incubated at 30° C. for one hour.

According to the method suggested by Lever, M. (Lever, M. (1972) *A new reaction for colorimetric determination of carbohydrates.* Anal. Biochem. 47, 273-279), 0.5N HCl solution (200 µl) containing 0.5% of 4-hydroxybenzhydrazide was added to the reaction solution, and thereafter, the solution was treated with boiling water for 5 minutes. The solution was cooled naturally, and then, a value at 410 nm was measured with a spectrophotometer, and an increase in the reducing power was calculated in terms of glucose, to be regarded as an activity value.

When cellulose, phosphate-swellable cellulose, paramylon, or alkali-swollen paramylon was used as a substrate, a reducing power of supernatant obtained by centrifugation after incubation was measured.

Figure 6:
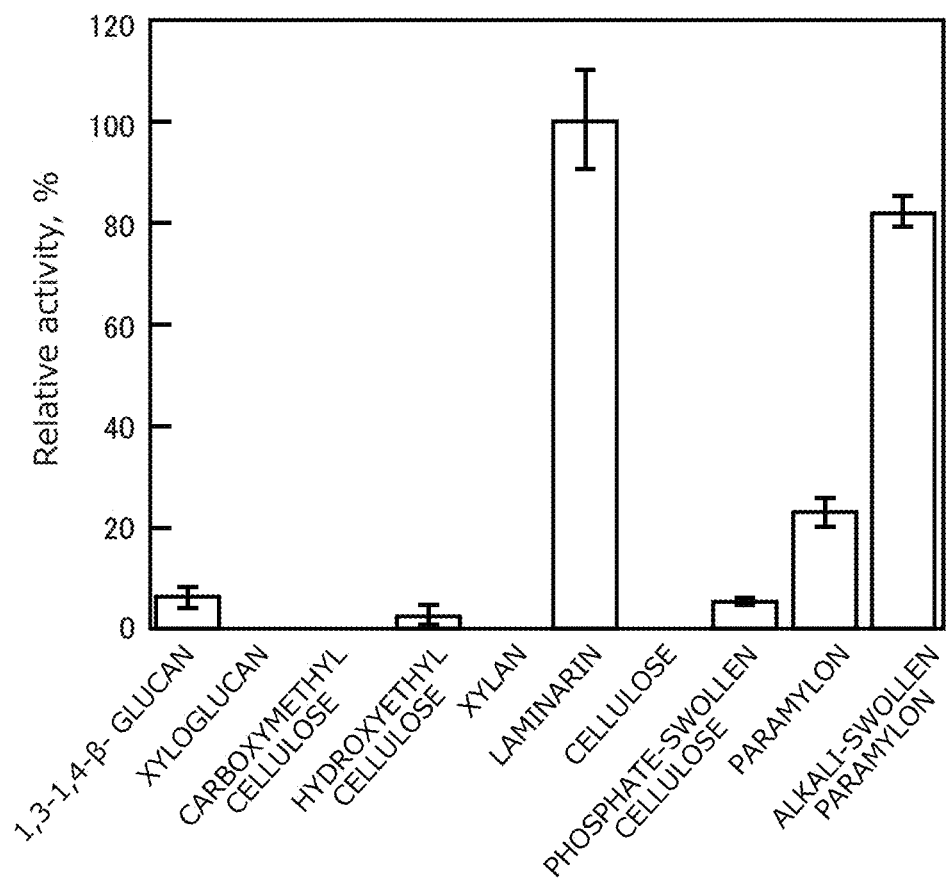
FIG. 6 is a graph showing substrate specificity of an enzyme EgCel17A, which is an example of the present invention.

The measurement results are shown in FIG. 6. In FIG. 6, decomposition activity with respect to laminarin is assumed to be 100, and relative activity mean values±SE (n=3) are shown.

According to FIG. 6, EgCel17A exhibited high decomposition activity with respect to laminarin, paramylon, and alkali-swollen paramylon.

Further, EgCel17A also exhibited decomposition activity with respect to 1,3-1,4-β-glucan, hydroxyethyl cellulose, and phosphate-swellable cellulose.

On the other hand, EgCel17A did not exhibit decomposition activity with respect to xyloglucan, carboxymethyl cellulose, xylan, and cellulose.

The decomposition activity with respect to paramylon was a little more than 20% of the decomposition activity with respect to laminarin, and the decomposition activity with respect to alkali-swollen paramylon was a little more than 80% of the decomposition activity with respect to laminarin, which proves that EgCel17A exhibits high decomposition activity with respect to paramylon and alkali-swollen paramylon, which is at a much higher level than that of a conventional enzyme.

The levels of decomposition activity of EgCel17A were as follows in the height descending order: laminarin>alkali-swollen paramylon>paramylon>1,3-1,4-β-glucan≈phosphate-swellable cellulose>hydroxyethyl cellulose.

It is clear from this result that EgCel17A, which is an endo-1,3-β-glucanase, decomposes laminarin, paramylon, and alkali-swollen paramylon, and hardly decomposes the other polysaccharides.

ii) Optimum Temperature

At different temperatures, decomposition activity of EgCel17A with respect to laminarin was examined, so that optimum temperature for EgCel17A was studied.

Figure 7:
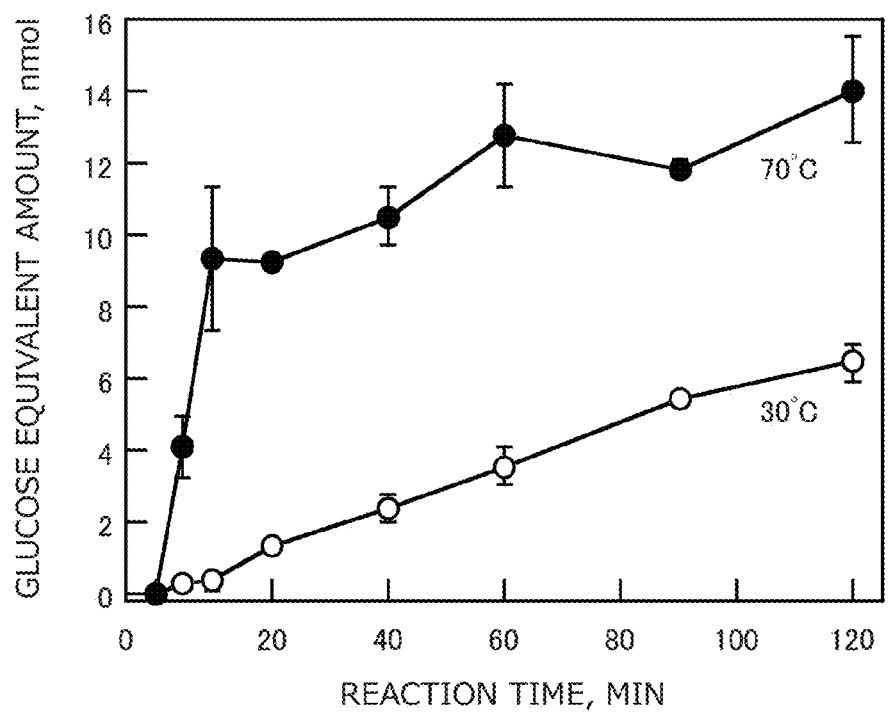
FIG. 7 is a graph showing optimum temperature for the enzyme EgCel17A, which is an example of the present invention.

The reaction solution containing 0.1% of laminarin, prepared in i) described above, was incubated at 30° C. and at 70° C. for 5 to 120 minutes. The results are shown in FIG. 7.

According to FIG. 7, in the decomposition of laminarin, in the case where the reaction was caused at 70° C., the maximum decomposition activity was exhibited 60 minutes later, which was about four times the decomposition activity in the reaction at 30° C.

Further, the reaction solution containing 0.1% of laminarin, prepared in i) described above, was incubated at 30° C., 40° C., 50° C., 60° C., and 70° C., for 1, 2, 3, 4, 5, 6, and 20 hours as to each temperature. As the activity values, mean values±SE (n=3) are indicated. The results are shown in FIG. 8.

Figure 8:
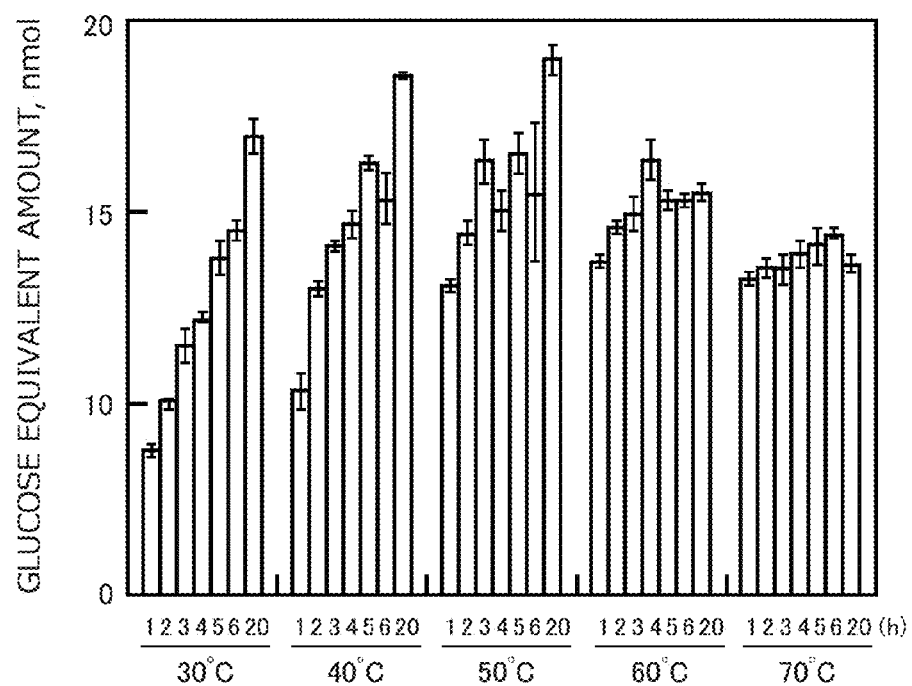
FIG. 8 is a graph showing laminarin decomposition activity in cases where the enzyme EgCel17A, which is an example of the present invention, was incubated at 30° C. to 70° C. for 1 to 20 hours.

It is clear from FIG. 8 that when a long-time enzyme reaction for 5 hours or longer was performed, the decomposition activity at 40° C. to 50° C. was higher than the decomposition activity at 70° C.

iii) Optimum pH

Laminarin decomposition activity of EgCel17A were examined at different pHs, so that optimum pH for EgCel17A was studied.

Figure 9:
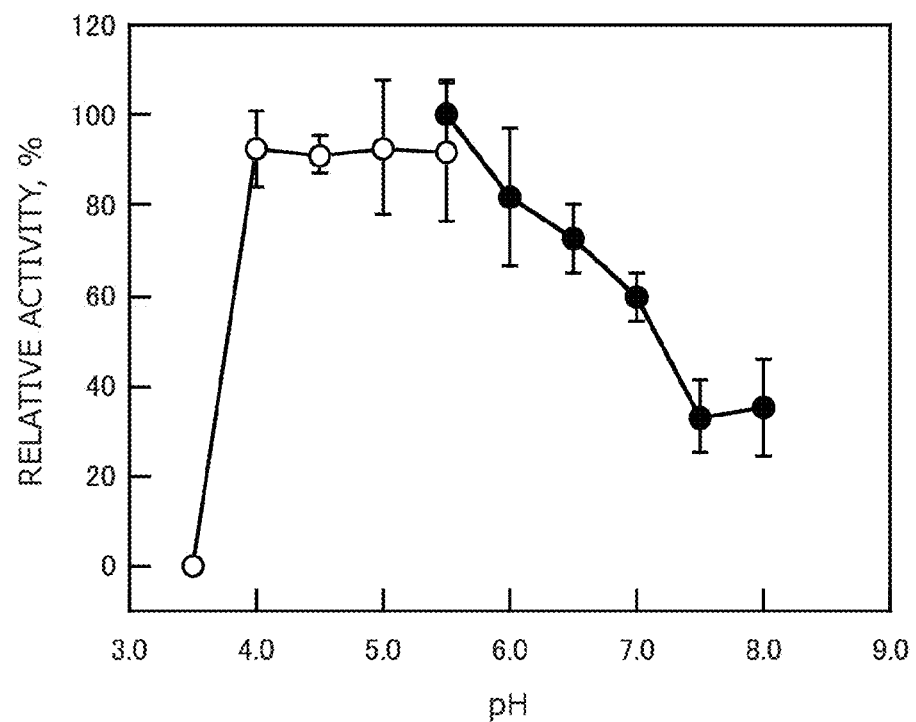
FIG. 9 is a graph showing optimum pH for the enzyme EgCel17A, which is an example of the present invention.

The reaction solution containing 0.1% of laminarin, prepared in i) described above, was incubated at pH 3.5 to 8.0. To adjust pH, sodium acetate (pH 3.5 to 5.5, white circles) and sodium phosphate (pH 5.5 to 8.0, black circles) were used. The results are shown in FIG. 9. As the activity values, mean values±SE (n=3) are indicated.

According to FIG. 9, high decomposition activity was observed at pH 3.7 to 7.0, in which particularly high decomposition activity was observed at pH 4.0 to 6.0.

iv) Comparison between Paramylon Decomposition Activity of EgCel17A and that of *Trichoderma* Cellulase Preparation Cellulase preparation of *Trichoderma* (*Trichoderma reesei* cellulase, Sigma-Aldrich Co., LLC), EgCel17A, and mixture of cellulase preparation of *Trichoderma* and EgCel17A were used so that paramylon decomposition activities were compared.

As samples of the cellulase preparation of *Trichoderma*, the same reaction solutions as the reaction solution prepared in i) described above containing 1% of paramylon except that µg and 10 µg of cellulase preparation of *Trichoderma*, respectively, were contained therein in place of the enzyme preparation were used.

Further, as samples of EgCel17A, the same reaction solutions as the reaction solution prepared in i) described above containing 1% of paramylon except that 0.4 µg, 2 µg, and 4 µg of EgCel17A prepared in Example 2, respectively, were contained therein in place of the enzyme preparation were used.

As samples of the mixture of the cellulase preparation of *Trichoderma* and EgCel17A, the same reaction solutions as the reaction solution prepared in i) described above containing 1% of paramylon except that the following were contained therein in place of the enzyme preparation were used: 2 µg of the cellulase preparation of *Trichoderma* and 0.4 µg of EgCel17A prepared in Example 2; 2 µg of the cellulase preparation of *Trichoderma* and 2 µg of EgCel17A prepared in Example 2; 2 µg of the cellulase preparation of *Trichoderma* and 4 µg of EgCel17A prepared in Example 2; 10 µg of the cellulase preparation of *Trichoderma* and 0.4 µg of EgCel17A prepared in Example 2; 10 µg of the cellulase preparation of *Trichoderma* and 2 µg of EgCel17A prepared in Example 2; 2 µg of the cellulase preparation of *Trichoderma* and 4 µg of EgCel17A prepared in Example 2.

Each sample was incubated at pH 5.5 (sodium acetate buffer), at temperature of 40° C., for 18 hours.

The results are shown in FIG. 10. As the activity values, mean values±SE (n=3) are indicated.

Consequently, the cellulase preparation of *Trichoderma* exhibited slight paramylon decomposition activity, but EgCel17A exhibited decomposition activity of about 100 times that of the cellulase preparation of *Trichoderma* at the same concentration (2 µg). Besides, the sample of 2 µg of EgCel17A exhibited decomposition activity at the same level as the sample of 10 µg of the cellulase preparation of *Trichoderma*.

iv) Comparison between Paramylon Decomposition Activity of EgCel17A and that of *Bacillus Subtilis* Glucanase Using glucanase derived from *Bacillus subtilis* (availed from Megazyme Inc.) and EgCel17A, decomposition activities with respect to paramylon were compared.

As samples of *bacillus subtilis* glucanase, the same reaction solutions as the reaction solution prepared in i) described above containing 1% of paramylon except that 2 µg and µg of *bacillus subtilis* glucanase, respectively, were contained therein in place of the enzyme preparation were used.

Further, as samples of EgCel17A, the same reaction solutions as the reaction solution prepared in i) described above containing 1% of paramylon except that 0.2 µg, 0.4 µg, 1 µg, 2 µg, and 4 µg of EgCel17A prepared in Example 2, respectively, were contained therein in place of the enzyme preparation were used.

Each sample was incubated at pH 5.5 (sodium acetate buffer), at temperature of 40° C., for 18 hours.

Figure 11:
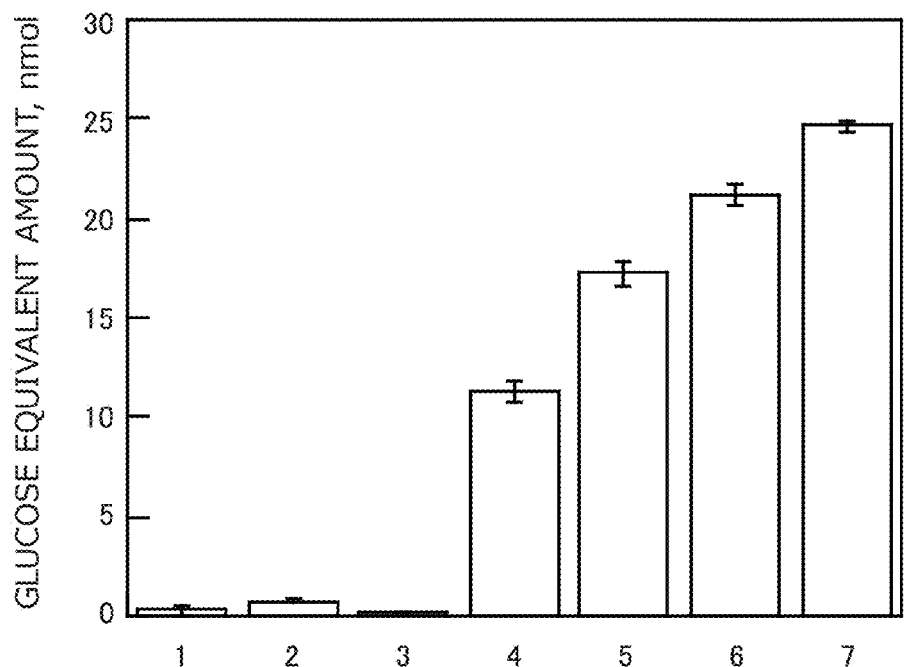
FIG. 11 is a graph showing paramylon decomposition activity of *bacillus subtilis* glucanase and the enzyme EgCel17A, which is an example of the present invention.

The results are shown in FIG. 11. As activity values, mean values±SE (n=3) are indicated.

Consequently, glucanase derived from *Bacillus subtilis* hardly decomposed paramylon, and only EgCel17A exhibited paramylon decomposition activity.

v) Influences Exerted by Bovine Serum Albumin (BSA) on Paramylon Decomposition Activity of EgCel17A Influences exerted by BSA on paramylon decomposition activity of EgCel17A were studied.

Samples were prepared that were obtained by using the same reaction solutions as the reaction solution prepared in i) described above containing 1% of paramylon except that 1.0 µg of EgCel17A prepared in Example 2 was added thereto in place of the enzyme preparation, and further by adding 0.2 µg, 5 µg, and 10 µg of BSA (Sigma-Aldrich Co., LLC) to the reaction solutions, respectively. These samples were incubated at pH 5.5 (sodium acetate buffer), at temperature of 40° C., for 18 hours.

Figure 12:
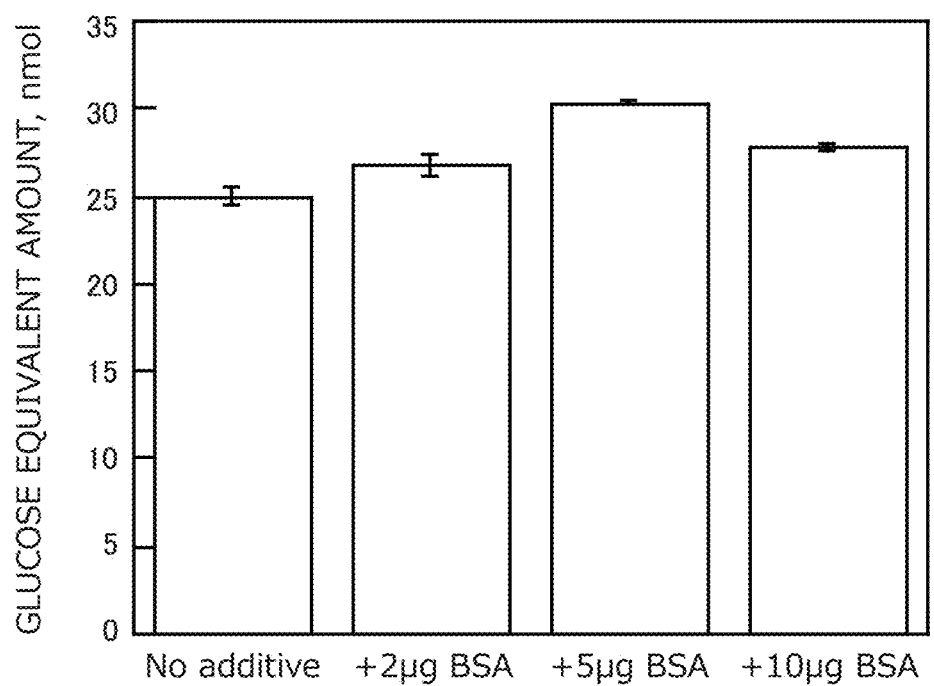
FIG. 12 is a graph showing influences exerted by the amount of added BSA on activity of the enzyme EgCel17A, which is an example of the present invention.

The results are shown in FIG. 12. As activity values, mean values±SE (n=3) are indicated.

Consequently, the sample to which 5 µg of BSA was added exhibited paramylon decomposition activity improved by about 10%, as compared with the sample to which no BSA was added.

BSA is known to have an effect of stabilizing and activating enzyme, and the contribution of the same to the improvement of paramylon decomposition activity of EgCel17A is about 10%, which is found to be lower as compared with the contribution thereof to other enzymes. This therefore makes it clear that when paramylon is decomposed using EgCel17A so that low-molecular-weight paramylon is to be produced, the necessity of adding BSA is lower as compared with the case where another decomposition enzyme is used.

vii) Influences Exerted by Metal on Paramylon Decomposition Activity of EgCel17A Influences exerted by metals on paramylon decomposition activity of EgCel17A were studied.

Metals were added to the same reaction solutions as the reaction solution prepared in i) described above containing 1% of paramylon except that 1.0 µg of EgCel17A prepared in Example 2 was added thereto in place of the enzyme preparation.

In other words, the following samples were prepared: no metal added sample; 10 mM NaCl added sample; 50 mM NaCl added sample; 100 mM NaCl added sample; 1 mM $MgCl_2$ added sample; 1 mM KCl added sample; 1 mM $CaCl_2$ added sample; 1 mM $FeSO_4$ added sample; 1 mM $MnCl_2$ added sample; 1 mM $ZnSO_4$ added sample; 1 mM $NiCl_2$ added sample; 1 mM $CuSO_4$ added sample; and 1 mM $CoCl_2$ added sample.

These samples were incubated at pH 5.5 (sodium acetate buffer), at temperature of 40° C., for 18 hours.

Figure 13:
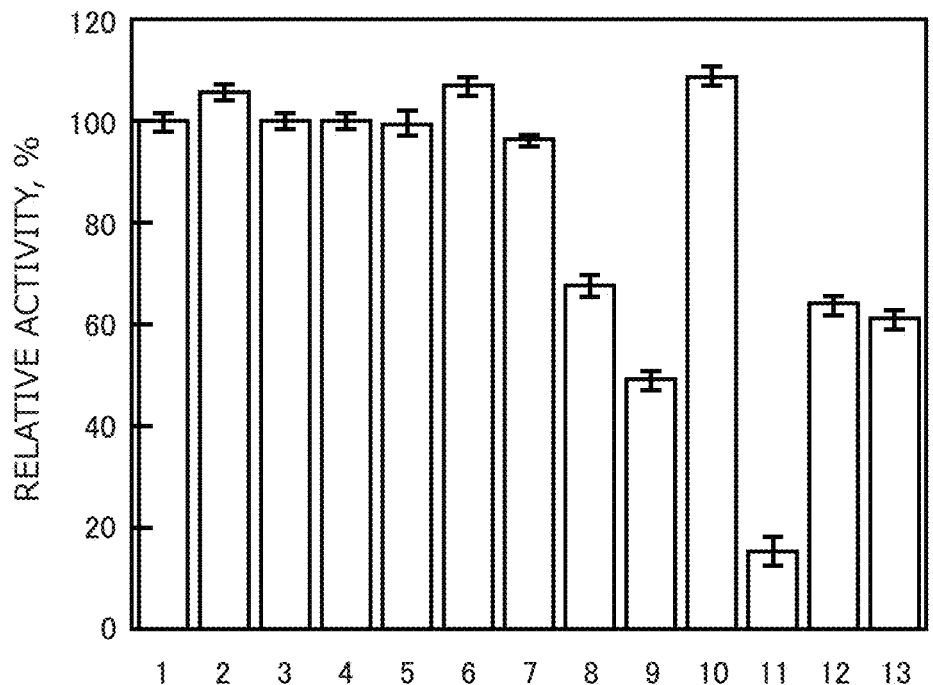
FIG. 13 is a graph showing influences exerted by the amount of added metal on activity of the enzyme EgCel17A, which is an example of the present invention.

The results are shown in FIG. 13. As activity values, mean values±SE (n=3) are indicated.

Consequently, the 10 mM NaCl added sample, the 1 mM KCl added sample, and the 1 mM $ZnSO_4$ added sample exhibited paramylon decomposition activities improved by about 10% as compared with the no metal added sample.

On the other hand, the 1 mM $CaCl_2$ added sample, the 1 mM $FeSO_4$ added sample, the 1 mM $MnCl_2$ added sample, the 1 mM $NiCl_2$ added sample, the 1 mM $CuSO_4$ added sample, and the 1 mM $CoCl_2$ added sample exhibited reduced paramylon decomposition activity as compared with the no metal added sample.

These results prove that in the case where metal ions of Ca, Fe, Mn, Ni, Cu, or Co are mixed in the reaction solution, the paramylon decomposition activity of EgCel17A decreases. It is clear that in the case where paramylon is to be decomposed by using EgCel17A so that low-molecular-weight paramylon is to be produced, a reaction solution or a culture medium in which the concentrations of these metal ions are reduced, or a reaction solution or a culture medium in which these metal ions are not mixed, may be used.

vii) Influences Exerted by Alkali Treatment to *Euglena* Containing Paramylon on Paramylon Decomposition Activity of EgCel17A Regarding alkali-swollen paramylon decomposition activity of EgCel17A, influences on the decomposition activity exerted by the concentration of alkali solution for pretreating *euglena* were studied.

*Euglena* powder suspended in water was treated with NaOH solutions having different concentrations (not treated with NaOH; treated with 0.025 M NaOH; treated with 0.05 M NaOH; treated with 0.25M NaOH; treated with 0.5 M NaOH; treated with 1 M NaOH; treated with 2 M NaOH; treated with 3 M NaOH; treated with 5 M NaOH), and neutralized with acetic acid, whereby alkali treated *euglena* was obtained.

Used were the same reaction solutions as the reaction solution prepared in i) described above except that 1 mg of the alkali treated *euglena* at respective treatment concentrations was added thereto in place of 1% alkali-swollen paramylon, and further, 1 µg of EgCel17A prepared in Example 2 was added as the enzyme preparation. Each sample was incubated at pH 5.5 (sodium acetate buffer), at temperature of 40° C., for three hours.

Figure 14:
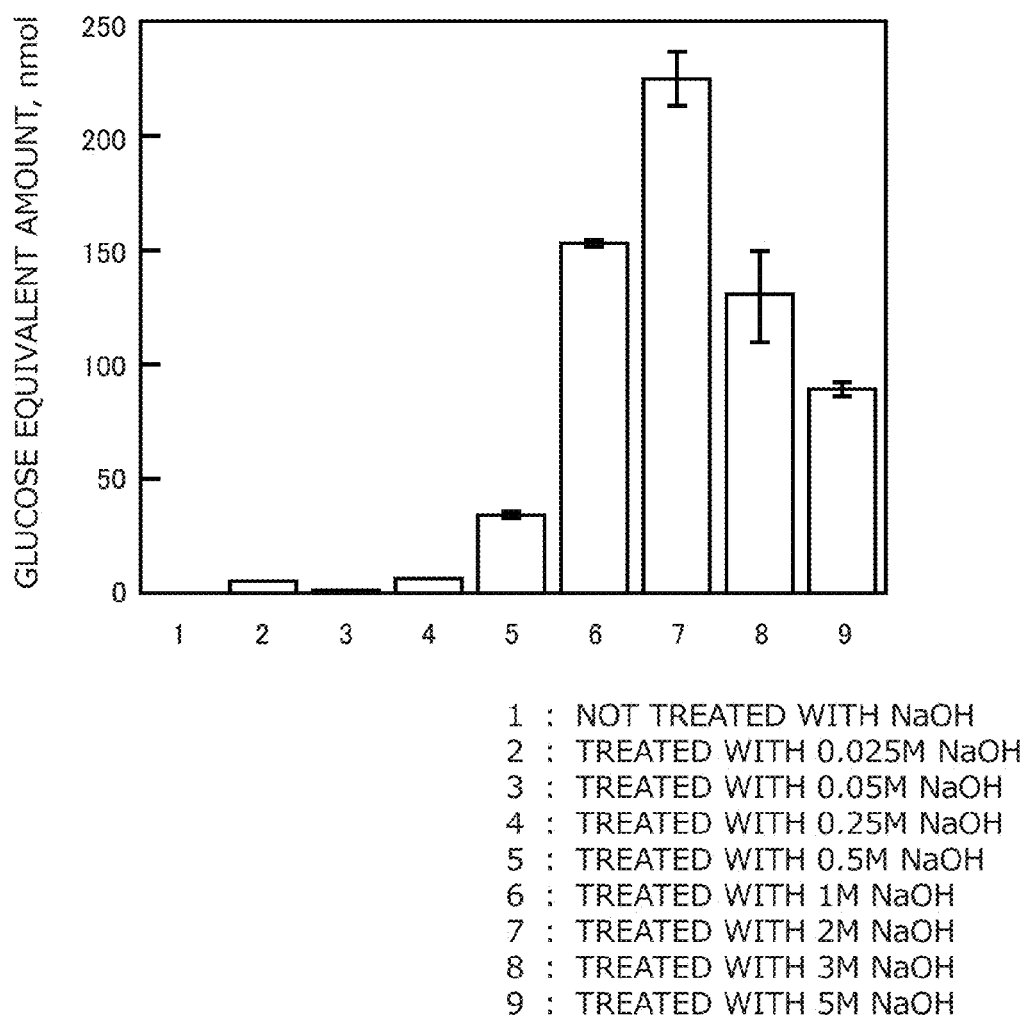
FIG. 14 is a graph showing influences exerted by conditions of an alkali treatment of *euglena* on activity of the enzyme EgCel17A, which is an example of the present invention.

The results are shown in FIG. 14. As the activity values, mean value±SE (n=3) are indicated.

Consequently, it is recognized that the treatment with NaOH of 0.5 M or more allowed EgCel17A to exhibit high decomposition activity. In particular, it is recognized that the treatment with 2 M NaOH resulted in the highest decomposition activity.

viii) Influences Exerted by NaCl on Paramylon Decomposition Activity of EgCel17A Influences exerted by sodium chloride on a reaction of decomposition of alkali-swollen paramylon by EgCel17A.

Used were the same reaction solutions as the reaction solution prepared in i) described above containing 1% alkali-swollen paramylon except that 1 µg of EgCel17A was added thereto in place of the enzyme preparation, and further, 0 M, 0.1 M, 0.5 M, 1.0 M, and 2.0 M of NaCl were added, respectively.

Each sample was incubated at pH 5.5 (sodium acetate buffer), at temperature of 40° C., for three hours.

Figure 15:
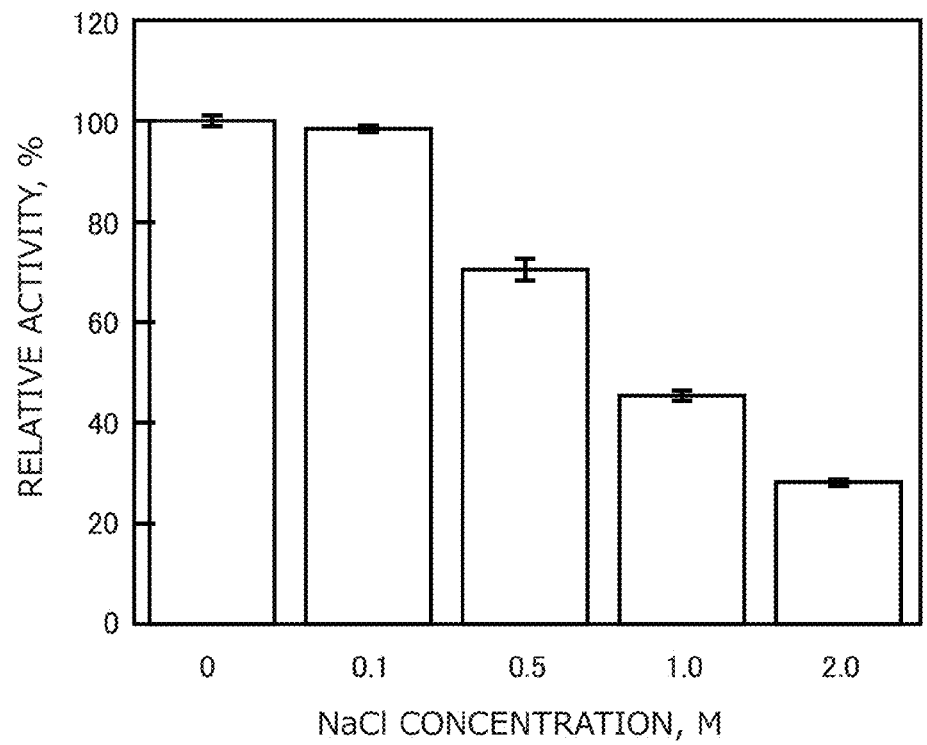
FIG. 15 is a graph showing influences exerted by the amount of added sodium chloride on activity of the enzyme EgCel17A, which is an example of the present invention.

The results are shown in FIG. 15. With the decomposition activity in the case where no NaCl is added being assumed to be 100, relative activity mean values±SE (n=3) are shown.

In FIG. 15, a decrease in the decomposition activity of EgCel17A in the presence of NaCl of 0.5 M or more is recognized. It is clear from this result that when paramylon is decomposed using EgCel17A so that low-molecular-weight paramylon is produced, the efficiency of production of low-molecular-weight paramylon is reduced due to NaCl. In the case where alkali treatment and neutralization of paramylon or *euglena* is performed as a pretreatment for the decomposition of paramylon by using EgCel17A, it is necessary to consider the influences of produced salts. It is therefore made clear that in the case where alkali treatment and neutralization of paramylon or *euglena* is performed as a pretreatment for the decomposition of paramylon by using EgCel17A, the NaCl concentration may be reduced, or NaCl may be removed, before EgCel17A is added.

Test Example 2

Transglycosylation Activity of EgCel17A

In the present test example, transglycosylation activity of EgCel17A was studied.

First of all, laminarioligosaccharides (availed from Megazyme Inc.) having polymerization degrees of 4 to 7 was labeled at a glucose residue on the reductive end side with Sulphorhodamine, according to the method suggested by Fry et al. (Fry S. C. (2002) *Novel 'dot-blot' assays for glycosyltransferases and glycosylhydrolases: optimization for xyloglucan endotransglycosylase (XET) activity*. Plant J. 11, 1141-1150.).

The fluorescent-labeled laminarioligosaccharides were purified by paper chromatography (solvent; butanol:acetic acid:water=1:1:1).

Using the fluorescent-labeled laminarioligosaccharides, transglycosylation activity of EgCel17A was examined.

Used were the same reaction solutions as the reaction solution prepared in i) of the test example 1 except that 0.1% of the fluorescent-labeled laminarioligosaccharides, or mixture of 0.1% of the fluorescent-labeled laminarioligosaccharides and 0.1% of laminarin was used therein in place of the substrate, and 0.2 µg of EgCel17A obtained in Example 2 was added in place of the enzyme preparation.

The samples were incubated at 40° C., for 0 minute (no incubation), 15 minutes, 30 minutes, and 60 minutes, respectively.

Figure 16:
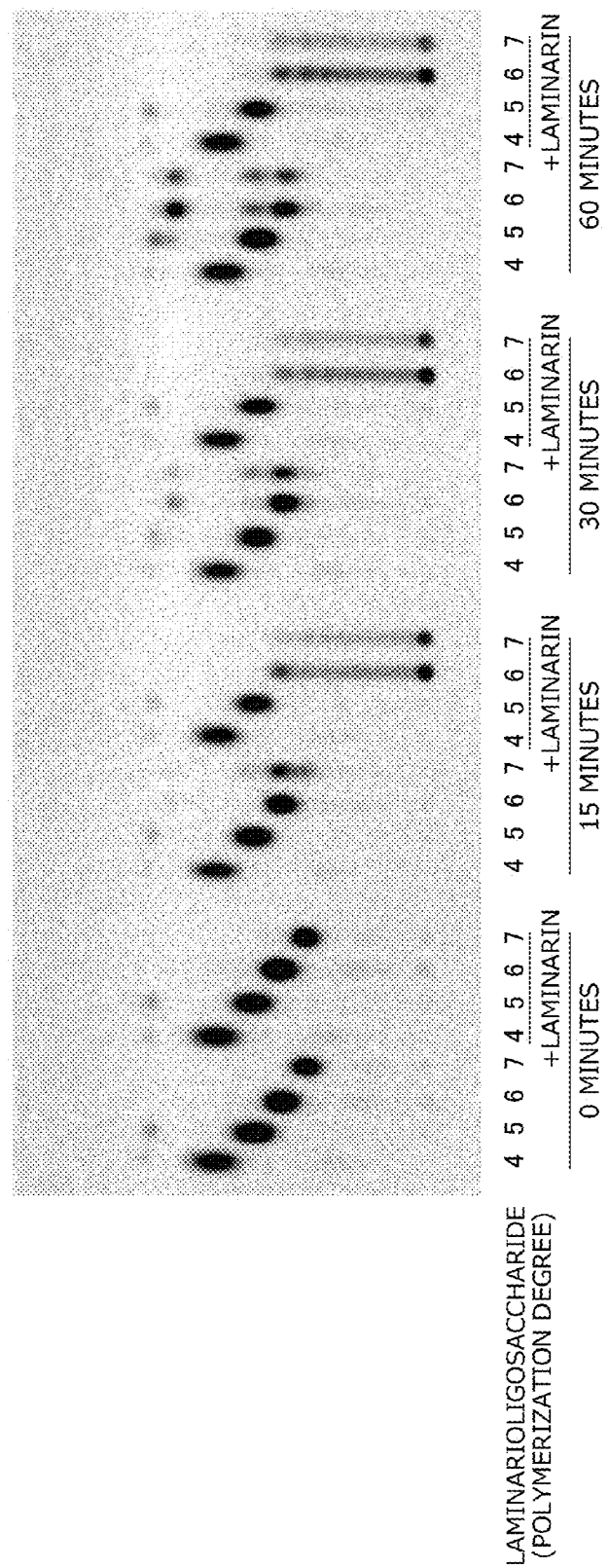
FIG. 16 shows results of paper chromatography, showing decomposition activity and transglycosylation activity of the enzyme EgCel17A, which is an example of the present invention, with respect to laminarin and laminarioligosaccharides.

The results are shown in FIG. 16.

As illustrated in FIG. 16, as time elapsed, fluorescence-labeled products having increased molecular weights were recognized in the reaction solutions containing laminarin as well as laminarihexaose (polymerization degree: 6) and laminariheptaose (polymerization degree: 7), respectively.

On the other hand, in the case where no laminarin was contained, as illustrated in FIG. 16, decomposition of laminarihexaose and laminariheptaose was recognized.

It is clear from these results that EgCel17A, after decomposing laminarin as a polymer, catalyzes a transfer reaction for transfer into fluorescence-labeled laminarihexaose and laminariheptaose.

Test Example 3

Method for Producing Glucose from Paramylon Using EgCel17A

Alkali-swollen paramylon and 100 mM phosphate buffer (pH5.5) were added to EgCel17A (1 µg) obtained in Example 2, which was followed by incubation at 40° C. for one hour. Then, a reaction product (1 µL) was applied to a HPLC column equilibrated with NaOH, and thereafter, the sodium acetate concentration (0 to 100 mM) was increased so that the reaction product was eluted.

Further, EgCel17A (1 µg) and MoCel3A (0.2 µg, (produced by the inventors of the present invention) Takahashi, M., Konishi T., Takeda T. (2011) *Biochemical characterization of Magnaporthe oryzae β-glucosidases for efficient β-glucan hydrolysis*. Appl. Microbiol. Biotechnol., 91, 1073-1082), which is a β-glucosidase derived from *Magnaporthe oryzae*, were mixed, and alkali-swollen paramylon and 100 mM phosphate buffer (pH5.5) were added thereto. The mixture was incubated at 40° C. for one hour, and thereafter, a reaction product was detected by HPLC.

The results are shown in FIG. 17.

As illustrated in FIG. 17, in the case where alkali-swollen paramylon was decomposed by EgCel17A alone, the peak of glucose was lower than the peaks of those having polymerization degrees of 3 and 4, but in the case where MoCel3A, which is β-glucosidase derived from *Magnaporthe oryzae*, was added to EgCel17A and alkali-swollen paramylon was decomposed with this, the peak of glucose was observed as indicating a main generation product.

What is described above makes it clear that mixing EgCel17A and MoCel3A enables to efficiently convert paramylon into glucose.

Test Example 4

Laminarioligosaccharide Decomposition and Transfer Reaction by EgCel17A

In the present test example, laminarioligosaccharide decomposition activity and transfer activity of EgCel17A were studied.

First of all, laminarioligosaccharides having polymerization degrees of 2 to 7 (100 µg), EgCel17A (0.1 µg), and a phosphate buffer (final concentration 100 mM, pH 5.5) were mixed, and were left to stand still at 40° C. After 0 hour, 0.5 hour, 1 hour, 2 hours, 4 hours, and 18 hours of reaction, samples were collected, and reaction products were separated by thin-layer chromatography. Here, as a solvent, a solvent of 1-butanol:acetic acid:water=2:1:1 was used. After development, it was dipped in sulfuric acid/ethanol (5:95) liquid containing 0.5% of thymol, and thereafter, treated for 5 minutes at 110° C.

Figure 18:
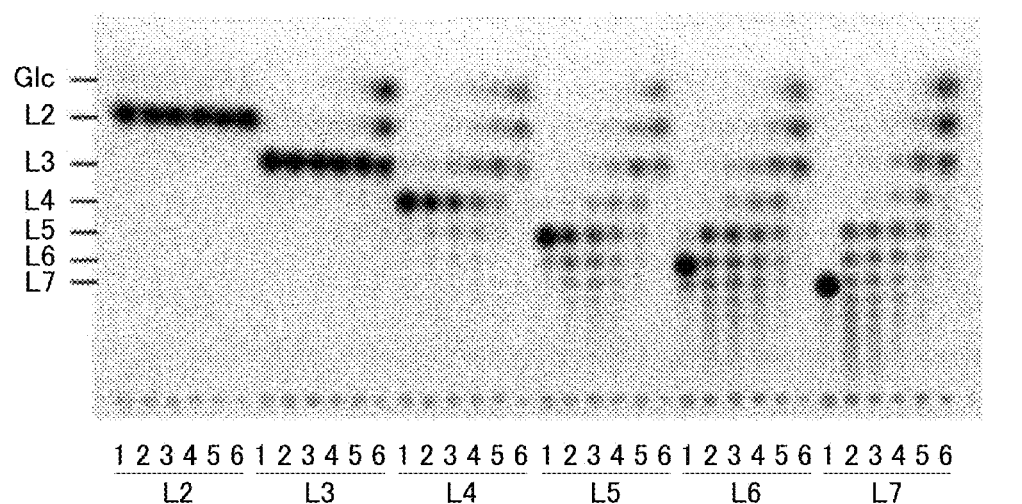
FIG. 18 shows results of thin-layer chromatography, showing decomposition activity and transfer activity of the enzyme EgCel17A, which is an example of the present invention, with respect to laminarioligosaccharides.

The results of separation of the reaction products by thin-layer chromatography are shown in FIG. 18.

As illustrated in FIG. 18, EgCel17A did not decompose laminaribiose (polymerization degree: 2), and decomposed laminarioligosaccharides having polymerization degrees of 3 to 7.

At the same time, as to laminarioligosaccharides having polymerization degrees of 3 to 7, and particularly those having polymerization degrees of 4 to 7, after 0.5 to 4 hours of reaction, laminarioligosaccharides having higher polymerization degrees were extracted, and a transfer reaction was caused to occur with respect to substrates of laminarioligosaccharides having polymerization degrees of 3 to 7, particularly those having polymerization degrees of 4 to 7.

As the reaction time elapsed to 18 hours, however, these substrates were decomposed to glucose, laminaribiose, and laminaritriose.

Example 5

Preparation of Recombinant Protein of EgCel81A and Determination of Activity Thereof i) Plasmid Construction A gene obtained by adding a secretion signal sequence of EGL2 (AB032830) derived from *Pisum sativum* to Egcel81A gene, and adding a histidine tag (His-tag) to a 3' terminal thereof was transfected into a pCambia plasmid vector. The plasmid vector thus constructed was transfected into *Agrobacterium* by electroporation, and thereafter, transgenic *Agrobacterium* was selected on a YEB plate (yeast extract 1 g/L, peptone 5 g/L, beef extract 5 g/L, sucrose 5 g/L, MgSO$_2$7H$_2$O 0.5 g/L) containing kanamycin.

ii) Gene Transfer to Rice Callus

Seeds of *Oryza sativa* (Sasanishiki) were sterilized, and inoculated in a C1 medium (N6-1-alanine 20 ml/L, N6-2-alanine 50 ml/L, N6-3-alanine 1 ml/L, N6-4-alanine 10 ml/L, N6-vitamin 1 ml/L, sucrose 3.75 g/L, casamino acid 0.3 g/L, proline 2.878 g/L, 2,4-dichloropfenoxyacetic acid (100 mg/L) 20 ml/L, gellan gum 3 g/L, (pH 5.8)), and was cultured at 30° C. for 5 days in a dark place, whereby callusing was induced. Rice calluses were mixed with *Agrobacterium*, spread over a K2 medium (N6-1-alanine ml/L, N6-2-alanine 50 ml/L, N6-3-alanine 1 ml/L, N6-4-alanine 10 ml/L, N6-vitamin 1 ml·L, sucrose 3.75 g, glucose 10 g/L, casamino acid 0.3 g/L, 2,4-dichloropfenoxyacetic acid (100 mg/L) 20 ml, gellan gum 3 g/L, (pH 5.2)), and was left to stand still for 3 days, at 25° C., in a dark place. After *Agrobacterium* was removed from collected rice calluses with a cleaning buffer, the rice calluses were inoculated in a K2 medium containing carbenicillin (400 μg/ml) and hygromycin (50 μg/ml), and cultured at 30° C. for 10 days. Thereafter, the rice calluses were inoculated in a K2 medium containing carbenicillin (300 μg/ml) and hygromycin (50 μg/ml), and gene transferred bodies were selected.

iii) Preparation of Protein

Regarding eight individual rice calluses, each rice callus (10 mg) was subjected to cell disruption in a buffer (50 mM sodium acetate (pH7.0), 300 mM sodium chloride), and thereafter, supernatant was collected by centrifugation (5,000 rpm, 5 min). The supernatant was concentrated and desalinized by ultrafiltration, and thereafter, the same was subjected to Western blotting and enzyme activity measurement.

iv) Western Blotting

Figure 19:
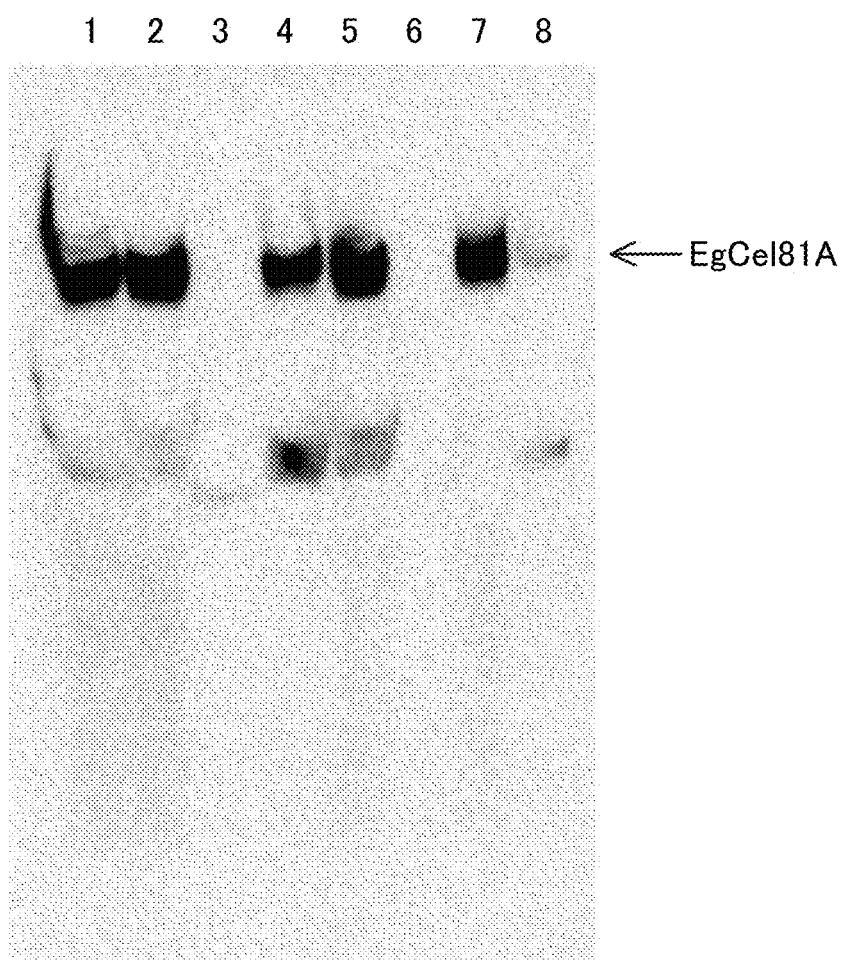
FIG. 19 is an image showing results of Western blotting of recombinant EgCel81A.

Proteins contained in the supernatant, after being separated by SDS-PAGE, were transcribed into PVDF membranes. Western blotting was performed using an antibody against the His-tag. The results of Western blotting performed on the eight individual rice calluses are shown in FIG. 19. The numbers 1 to 8 in FIG. 19 indicate the eight individual rice calluses, respectively.

v) Enzyme Activity

Figure 20:
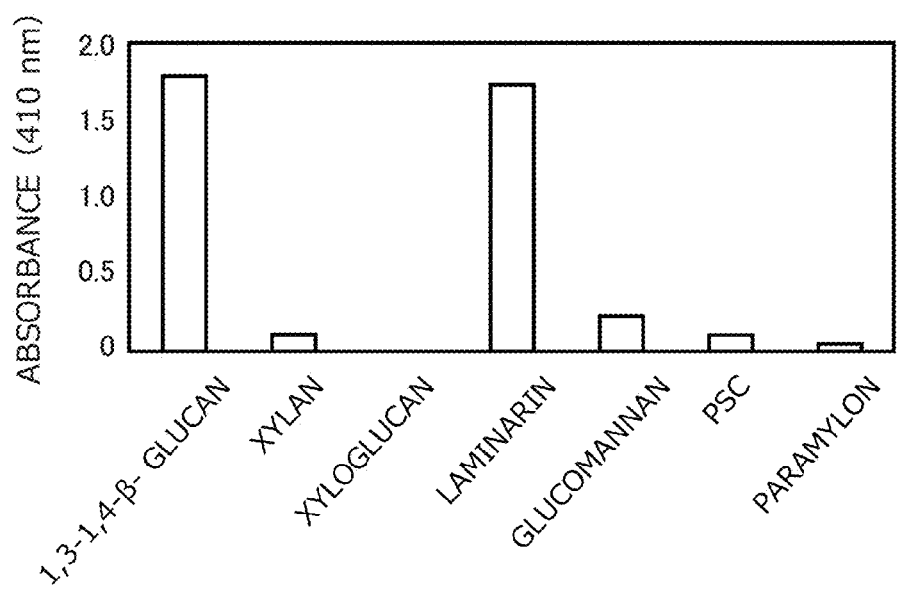
FIG. 20 is a graph showing results of hydrolysis activity measurement tests with respect to respective polysaccharides of the recombinant EgCel81A.

Seven types of polysaccharide substrates (1,3-1,4-βglucan, xylan, xyloglucan, laminarin, glucomannan, PSC (phosphate-swellable cellulose), and paramylon), 0.1% each, and acetic acid buffer (100 mM acetic acid buffer (pH6.0)) were added to supernatant derived from rice callus of No. 1 in FIG. 19, whose signal was detected by Western blotting, and were left to stand still at 30° C. for 18 hours. To each reaction solution, p-hydroxybenzoic acid hydrazide was added, and the reaction solutions were boiled for 5 minutes. Then, absorbances at 410 nm were measured, whereby increased reducing powers were determined. The measurement results are shown in FIG. 20.

vi) Result

As described above, proteins were prepared from eight individual rice calluses, and Western blotting was performed by using an antibody against the His-tag. As a result, as illustrated in FIG. 19, five individual rice calluses (Nos. 1, 2, 4, 5, and 7), recognized to have produced EgCel81A, were obtained.

Further, using protein prepared from the rice callus (No. 1), hydrolysis activity was examined. As a result, as illustrated in FIG. 20, hydrolysis activity with respect to 1,3-1, 4-β-glucan and laminarin was remarkably recognized. As β-1,3-bonds are included commonly in these polysaccharides, it was clarified that EgCel81A was an endo-1,3-β-glucanase.

The invention claimed is:

1. An isolated endo-1,3-β-glucanase comprising the amino acid having at least 90% identity to SEQ ID NO: 2 and contains at least one deletion, substitution, or addition relative to SEQ ID NO: 2, and having an endo-type hydrolysis activity of hydrolyzing a β-1,3-bond of a β-1,3-glucan.

2. The endo-1,3-β-glucanase according to claim 1, further exhibiting the following properties:
   (1) substrate specificity: decomposing at least paramylon;
   (2) decomposition activity: a ratio of paramylon decomposition activity with respect to laminarin decomposition activity is 20% or higher;
   (3) optimum pH: 3.7 to 7.0;
   (4) optimum temperature: 30° C. to 70° C.; and
   (5) decomposition activity: a ratio of paramylon decomposition activity with respect to alkali-swollen paramylon decomposition activity is 25% or higher.

3. The endo-1,3-β-glucanase according to claim 2, wherein the endo-1,3-β-glucanase additionally has a substrate specificity of decomposing alkali-swollen paramylon and laminarin, and
an optimum temperature during a reaction time up to one hour is 50° C. or higher, an optimum temperature during a reaction time from one hour up to two hours is 40° C. or higher, and an optimum temperature during a reaction time of 20 hours or more is 60° C. or lower.

4. An enzyme preparation for reducing a molecular weight of paramylon, the enzyme preparation containing the endo-1,3-β-glucanase according to claim 1.

5. A method for producing low-molecular-weight paramylon, the method comprising:
allowing the endo-1,3-β-glucanase according to claim 1 to act on paramylon, to generate the low-molecular-weight paramylon.

6. The method for producing the low-molecular-weight paramylon according to claim 5,
wherein a glucosidase, together with the endo-1,3-β-glucanase, is allowed to act on the paramylon, so that glucose is generated as a main product of the low-molecular-weight paramylon.

7. An isolated endo-1,3-β-glucanase comprising the amino acid having at least 90% identity to SEQ ID NO: 2 and contains at least one deletion, substitution, or addition relative to SEQ ID NO: 2.

* * * * *

SEQUENCE LISTING

<160> NUMBER OF SEQ ID NOS: 13

<210> SEQ ID NO 1
<211> LENGTH: 1611
<212> TYPE: DNA
<213> ORGANISM: Euglena gracilis Z
<220> FEATURE:
<221> NAME/KEY: CDS
<222> LOCATION: (35)..(1240)

<400> SEQUENCE: 1
gaaaacactt tctgagtgtc tattttttt cggg atg att cgc ctt ttg ggt ctg     55
                                  Met Ile Arg Leu Leu Gly Leu
                                   1               5

```
gca ttg ttg gca tgc aca agc cac gcc acg gag ctg gga tgg aat atc       103
Ala Leu Leu Ala Cys Thr Ser His Ala Thr Glu Leu Gly Trp Asn Ile
        10              15                  20 aac ttc ggc ttc cag caa aat ccg ctg aac ccg gat gtt gcg gtt gca       151
Asn Phe Gly Phe Gln Gln Asn Pro Leu Asn Pro Asp Val Ala Val Ala
25                  30                  35 aaa ttg aag tcc ctc att cca cag ctg aac tat tcc aag acg ttc gac       199
Lys Leu Lys Ser Leu Ile Pro Gln Leu Asn Tyr Ser Lys Thr Phe Asp
40                  45                  50                  55 tac aat gca aca gtg ttg gca gca ttg cac aca cat gga att cgt aac       247
Tyr Asn Ala Thr Val Leu Ala Ala Leu His Thr His Gly Ile Arg Asn
                60                  65                  70 atg gtc gtt ggc att ccc aac tcc gac ctg caa agt att gca aca agt       295
Met Val Val Gly Ile Pro Asn Ser Asp Leu Gln Ser Ile Ala Thr Ser
            75                  80                  85 gga aac ccc ctg gtg gga acg atc ctt gat ggg ctg aag cca ctg tac       343
Gly Asn Pro Leu Val Gly Thr Ile Leu Asp Gly Leu Lys Pro Leu Tyr
        90                  95                  100 gat gac ggt gtc caa ctc acc atc gcc gtg ggg aac gaa cca acc ctt       391
Asp Asp Gly Val Gln Leu Thr Ile Ala Val Gly Asn Glu Pro Thr Leu
    105                 110                 115 gcc act tat gga act gca tac tcc cct tgg gtg tat cct gcc ctg ctc       439
Ala Thr Tyr Gly Thr Ala Tyr Ser Pro Trp Val Tyr Pro Ala Leu Leu
120                 125                 130                 135 aat gtc cgc tcc aca ttg tcc aac aag tac atg aac aaa gtc aaa ttg       487
Asn Val Arg Ser Thr Leu Ser Asn Lys Tyr Met Asn Lys Val Lys Leu
                140                 145                 150 act gtc ccc ttc gat tcc ggc atc ctt ggg acc agc tat ccg ccc agc       535
Thr Val Pro Phe Asp Ser Gly Ile Leu Gly Thr Ser Tyr Pro Pro Ser
            155                 160                 165 cag gga att ttt tca atc agc aca gcc agt gtt gtc acc acc gtt gca       583
Gln Gly Ile Phe Ser Ile Ser Thr Ala Ser Val Val Thr Thr Val Ala
        170                 175                 180 gaa ttt ctg aag aat gaa ggg tca cct ttc act gtg aac ctg tat cct       631
Glu Phe Leu Lys Asn Glu Gly Ser Pro Phe Thr Val Asn Leu Tyr Pro
    185                 190                 195 ttc ttc tca ctg gtt gac aac ccc act gat gtg agt gtt gct tat gct       679
Phe Phe Ser Leu Val Asp Asn Pro Thr Asp Val Ser Val Ala Tyr Ala
200                 205                 210                 215 aca ttg cag act ggc ctc act gcc tcg gat ggc atc acg tac ccc aac       727
Thr Leu Gln Thr Gly Leu Thr Ala Ser Asp Gly Ile Thr Tyr Pro Asn
                220                 225                 230 atg ctg gcg gcg atg gtg gct gct gtg cgc gct gcg ctg ttg cac cag       775
Met Leu Ala Ala Met Val Ala Ala Val Arg Ala Ala Leu Leu His Gln
            235                 240                 245 gac cca gtc ctg aca gag gca aac ttg ccc atc att gtc ggt gag act       823
Asp Pro Val Leu Thr Glu Ala Asn Leu Pro Ile Ile Val Gly Glu Thr
        250                 255                 260 ggc tgg cca act tca ggc aac acc tac gcc acg gtg gaa aac gcc cag       871
Gly Trp Pro Thr Ser Gly Asn Thr Tyr Ala Thr Val Glu Asn Ala Gln
    265                 270                 275 acg tac gtc aac aac gcc gtc aac tgc ggg att ccg ctg tat ggc ttc       919
Thr Tyr Val Asn Asn Ala Val Asn Cys Gly Ile Pro Leu Tyr Gly Phe
280                 285                 290                 295 gag gcc ttc gac gag aag ctg aag acg agc ggc agc ggc agc gga tcc       967
Glu Ala Phe Asp Glu Lys Leu Lys Thr Ser Gly Ser Gly Ser Gly Ser
                300                 305                 310 acc agt tct gtt gag ggc agc tgg gga tgg atg tca gag gga ggc gac      1015
Thr Ser Ser Val Glu Gly Ser Trp Gly Trp Met Ser Glu Gly Gly Asp
            315                 320                 325
```

```
ccc aag ttt ccc atc aac tgg ccc acg gga cca gtg gcg cca gcg gag     1063
Pro Lys Phe Pro Ile Asn Trp Pro Thr Gly Pro Val Ala Pro Ala Glu
        330                 335                 340 acg tgc gat tcc aaa ttc cca cct gcc act gga gag ttc gtg aaa ctt     1111
Thr Cys Asp Ser Lys Phe Pro Pro Ala Thr Gly Glu Phe Val Lys Leu
345                 350                 355 gtt tgc cca ccc aac acc ctc gca ggg tgg ttg caa tct ggc tct tgt     1159
Val Cys Pro Pro Asn Thr Leu Ala Gly Trp Leu Gln Ser Gly Ser Cys
360                 365                 370                 375 cag cag gat tcg gac tgc gat gtc atc tcc tgc ccc gag gtg ccc aag     1207
Gln Gln Asp Ser Asp Cys Asp Val Ile Ser Cys Pro Glu Val Pro Lys
            380                 385                 390 gat acg gtg gtg gcc acc tgt tcc agc gtc taa agcggggacc agctgcgttc   1260
Asp Thr Val Val Ala Thr Cys Ser Ser Val
                395                 400 tggggtagcg cctcttttcg cataaggcat gggcatgtaa acctcctccc tggtctctga   1320
caaatgtatg tatgctctgc tgaatcaatg tcgtgtgcgc tccgtgaggg ctcctttggg   1380
gtcttacacc aaattgcgca gtggcgttgc aagaaagcgg agcaccaaca ggcgcttggg   1440
gcccccactc acccgagggt ccggcaagtt gccacacaac aacggccagt gttcaactgc   1500
tttatcccaa agttcagaaa cgctctctcc ctccccatat accacgtcat tccagctgcg   1560
acatttcccc ggttgcgttt ttttgaaaaa aaaaaaaaa aaaaaaaaaa a             1611

<210> SEQ ID NO 2
<211> LENGTH: 401
<212> TYPE: PRT
<213> ORGANISM: Euglena gracilis Z

<400> SEQUENCE: 2

Met Ile Arg Leu Leu Gly Leu Ala Leu Leu Ala Cys Thr Ser His Ala
1               5                   10                  15

Thr Glu Leu Gly Trp Asn Ile Asn Phe Gly Phe Gln Gln Asn Pro Leu
            20                  25                  30

Asn Pro Asp Val Ala Val Ala Lys Leu Lys Ser Leu Ile Pro Gln Leu
        35                  40                  45

Asn Tyr Ser Lys Thr Phe Asp Tyr Asn Ala Thr Val Leu Ala Ala Leu
    50                  55                  60

His Thr His Gly Ile Arg Asn Met Val Val Gly Ile Pro Asn Ser Asp
65                  70                  75                  80

Leu Gln Ser Ile Ala Thr Ser Gly Asn Pro Leu Val Gly Thr Ile Leu
                85                  90                  95

Asp Gly Leu Lys Pro Leu Tyr Asp Asp Gly Val Gln Leu Thr Ile Ala
            100                 105                 110

Val Gly Asn Glu Pro Thr Leu Ala Thr Tyr Gly Thr Ala Tyr Ser Pro
        115                 120                 125

Trp Val Tyr Pro Ala Leu Leu Asn Val Arg Ser Thr Leu Ser Asn Lys
    130                 135                 140

Tyr Met Asn Lys Val Lys Leu Thr Val Pro Phe Asp Ser Gly Ile Leu
145                 150                 155                 160

Gly Thr Ser Tyr Pro Pro Ser Gln Gly Ile Phe Ser Ile Ser Thr Ala
                165                 170                 175

Ser Val Val Thr Thr Val Ala Glu Phe Leu Lys Asn Glu Gly Ser Pro
            180                 185                 190

Phe Thr Val Asn Leu Tyr Pro Phe Phe Ser Leu Val Asp Asn Pro Thr
        195                 200                 205
```

-continued

```
Asp Val Ser Val Ala Tyr Ala Thr Leu Gln Thr Gly Leu Thr Ala Ser
    210                 215                 220
Asp Gly Ile Thr Tyr Pro Asn Met Leu Ala Ala Met Val Ala Ala Val
225                 230                 235                 240
Arg Ala Ala Leu Leu His Gln Asp Pro Val Leu Thr Glu Ala Asn Leu
                245                 250                 255
Pro Ile Ile Val Gly Glu Thr Gly Trp Pro Thr Ser Gly Asn Thr Tyr
            260                 265                 270
Ala Thr Val Glu Asn Ala Gln Thr Tyr Val Asn Asn Ala Val Asn Cys
        275                 280                 285
Gly Ile Pro Leu Tyr Gly Phe Glu Ala Phe Asp Glu Lys Leu Lys Thr
    290                 295                 300
Ser Gly Ser Gly Ser Gly Ser Thr Ser Ser Val Glu Gly Ser Trp Gly
305                 310                 315                 320
Trp Met Ser Glu Gly Gly Asp Pro Lys Phe Pro Ile Asn Trp Pro Thr
                325                 330                 335
Gly Pro Val Ala Pro Ala Glu Thr Cys Asp Ser Lys Phe Pro Pro Ala
            340                 345                 350
Thr Gly Glu Phe Val Lys Leu Val Cys Pro Pro Asn Thr Leu Ala Gly
        355                 360                 365
Trp Leu Gln Ser Gly Ser Cys Gln Gln Asp Ser Asp Cys Asp Val Ile
    370                 375                 380
Ser Cys Pro Glu Val Pro Lys Asp Thr Val Val Ala Thr Cys Ser Ser
385                 390                 395                 400
Val
```

<210> SEQ ID NO 3
<211> LENGTH: 3119
<212> TYPE: DNA
<213> ORGANISM: Euglena gracilis Z
<220> FEATURE:
<221> NAME/KEY: CDS
<222> LOCATION: (60)..(3002)

<400> SEQUENCE: 3

```
gaaggagtag aaaacacttt ctgagtgtct attttttttc gggcggcggg cggtccgcc      59 atg cgg tgg gtc ctc ccg ctc tgc ctg gcc ctc cta tcc gcg ccg ggg      107
Met Arg Trp Val Leu Pro Leu Cys Leu Ala Leu Leu Ser Ala Pro Gly
1               5                   10                  15 acg gcg gac ctc tgc acg tac ttc gcc cgg cag cgg ctt gtc gac ttc      155
Thr Ala Asp Leu Cys Thr Tyr Phe Ala Arg Gln Arg Leu Val Asp Phe
                20                  25                  30 ccc gac gtc ctc gtc atg ccc gtc ccg gac aac gcc gcc tgt tgc ggc      203
Pro Asp Val Leu Val Met Pro Val Pro Asp Asn Ala Ala Cys Cys Gly
            35                  40                  45 gtc tgt ctc gcc acg ccg gcc tgc act gta tcc gtg ctg acc aat acg      251
Val Cys Leu Ala Thr Pro Ala Cys Thr Val Ser Val Leu Thr Asn Thr
        50                  55                  60 agt tgc cat ctg aag cgc ttc aac atg acg gtg gac aac aaa acc ctg      299
Ser Cys His Leu Lys Arg Phe Asn Met Thr Val Asp Asn Lys Thr Leu
65                  70                  75                  80 cgt gct gac cct aac tcc gtc gtc tgc gtc ccc ctg ccc aag ccc ggc      347
Arg Ala Asp Pro Asn Ser Val Val Cys Val Pro Leu Pro Lys Pro Gly
                85                  90                  95 cag ggg ccc gcc ggc gcc tcc tac ccg ccc ctc ccc aag ccc acc att      395
Gln Gly Pro Ala Gly Ala Ser Tyr Pro Pro Leu Pro Lys Pro Thr Ile
            100                 105                 110
```

```
cgg gac aac gcc acc ttc ccg gct gcc tcg cgg ctg gac agc ggc ttc    443
Arg Asp Asn Ala Thr Phe Pro Ala Ala Ser Arg Leu Asp Ser Gly Phe
        115                 120                 125 cca cgc ctc tcg atg gag aac ccg gaa aag ctc ggc ttc ccg ggc atc    491
Pro Arg Leu Ser Met Glu Asn Pro Glu Lys Leu Gly Phe Pro Gly Ile
130                 135                 140 gct cgg gat ggc ttc gcc gcg ccc aat gtc gac aag atg tgt ctc ccg    539
Ala Arg Asp Gly Phe Ala Ala Pro Asn Val Asp Lys Met Cys Leu Pro
145                 150                 155                 160 aaa ggc cgg ccg ttc ccg ctg ccc acc aac gac tgg tgg gtg cca atc    587
Lys Gly Arg Pro Phe Pro Leu Pro Thr Asn Asp Trp Trp Val Pro Ile
                165                 170                 175 att cgg cca acg ccg gag acc acc ttg aat tat atc ttt cct gtc cct    635
Ile Arg Pro Thr Pro Glu Thr Thr Leu Asn Tyr Ile Phe Pro Val Pro
            180                 185                 190 tat atc tat gac atg ttc ccg gca ggg ttc cac ctc gcc tat ccg ttc    683
Tyr Ile Tyr Asp Met Phe Pro Ala Gly Phe His Leu Ala Tyr Pro Phe
        195                 200                 205 atc att acg tcc ccc aat tca gtc cgc aat atc atc aac cgc tat tgg    731
Ile Ile Thr Ser Pro Asn Ser Val Arg Asn Ile Ile Asn Arg Tyr Trp
210                 215                 220 acc gtc acg gcg gag gga gcg gat gag gca tcc tcc agc tat tgt gtg    779
Thr Val Thr Ala Glu Gly Ala Asp Glu Ala Ser Ser Ser Tyr Cys Val
225                 230                 235                 240 cgg cac ttc gac gag ctg act gcc acc gtg gcg tgg cgt gcc acc acc    827
Arg His Phe Asp Glu Leu Thr Ala Thr Val Ala Trp Arg Ala Thr Thr
                245                 250                 255 aac cag tcc atg atg gag atg ccc atc gtt cgg ggt tcc ccg tac gcc    875
Asn Gln Ser Met Met Glu Met Pro Ile Val Arg Gly Ser Pro Tyr Ala
            260                 265                 270 acc gtc aag tat ttc cag gcg cag ccc aag ctg tcc act gcg cag aag    923
Thr Val Lys Tyr Phe Gln Ala Gln Pro Lys Leu Ser Thr Ala Gln Lys
        275                 280                 285 gtg cgg gcc ttc ttt gtg gac ggc gtg cgc cgc aac tgc tca ggc gat    971
Val Arg Ala Phe Phe Val Asp Gly Val Arg Arg Asn Cys Ser Gly Asp
290                 295                 300 tcc ttc ccg ggg cac aag ttc act gtg tgg ctg ctt gac agt gac gag    1019
Ser Phe Pro Gly His Lys Phe Thr Val Trp Leu Leu Asp Ser Asp Glu
305                 310                 315                 320 gag tgg cag ttc tgg gtg ccc ccc ggc acg ccg gtg gtc tgc caa gtg    1067
Glu Trp Gln Phe Trp Val Pro Pro Gly Thr Pro Val Val Cys Gln Val
                325                 330                 335 gcg gtg gag cgg ggg atg ccc gcc gtg gtg gtc agc gtg gct gac ccg    1115
Ala Val Glu Arg Gly Met Pro Ala Val Val Val Ser Val Ala Asp Pro
            340                 345                 350 gcc ttc tcg ggc tgg gtc cgc ctg gcc ctc agc aac aac tgc acc acg    1163
Ala Phe Ser Gly Trp Val Arg Leu Ala Leu Ser Asn Asn Cys Thr Thr
        355                 360                 365 ggg atg gtc ccg ccc tcc ccg cac tgc gtt cag gag ggc atg gcg aac    1211
Gly Met Val Pro Pro Ser Pro His Cys Val Gln Glu Gly Met Ala Asn
370                 375                 380 gaa gac atg gag gac tac agc caa gcc ctg gac acc ggc agc aat gcc    1259
Glu Asp Met Glu Asp Tyr Ser Gln Ala Leu Asp Thr Gly Ser Asn Ala
385                 390                 395                 400 tgc ccc atg aag ggt aag gtg ggc atg cgg gcc acc ggg cgg cag atg    1307
Cys Pro Met Lys Gly Lys Val Gly Met Arg Ala Thr Gly Arg Gln Met
                405                 410                 415 gag tat att ctg gag tgg gag gtg gcc cac tgc tgg tcc ccg tcg ttc    1355
Glu Tyr Ile Leu Glu Trp Glu Val Ala His Cys Trp Ser Pro Ser Phe
            420                 425                 430
```

```
                                                      -continued ttc cag tcc agc tcc ctg ctg ctg att gcc ttg ccg cac cat atg gcg    1403
Phe Gln Ser Ser Ser Leu Leu Leu Ile Ala Leu Pro His His Met Ala
            435                 440                 445 aag atg caa gat ggg ttc acc aag att gtt cct act ggg ggc cac cgc    1451
Lys Met Gln Asp Gly Phe Thr Lys Ile Val Pro Thr Gly Gly His Arg
450                 455                 460 aac acc cgc ggg tat aac acc ccc gtc caa acg ccc cac aac cgg tgg    1499
Asn Thr Arg Gly Tyr Asn Thr Pro Val Gln Thr Pro His Asn Arg Trp
465                 470                 475                 480 gtg ctg gag atc cag cgc acg gcc ctg ggc tgg gtg gag acg ccc gac    1547
Val Leu Glu Ile Gln Arg Thr Ala Leu Gly Trp Val Glu Thr Pro Asp
                485                 490                 495 gcg agg cgg ctc gac ttc ctc cgc acg tac ctc gtc aac aac gac agc    1595
Ala Arg Arg Leu Asp Phe Leu Arg Thr Tyr Leu Val Asn Asn Asp Ser
            500                 505                 510 cac ttc gac ctg ccg ccc gac gtg cag cgc ggc tac atc gac ccc tac    1643
His Phe Asp Leu Pro Pro Asp Val Gln Arg Gly Tyr Ile Asp Pro Tyr
        515                 520                 525 aac gcc ggg aag gag atg tcc cga ctg gcc cgt ctg gtc atc atc gca    1691
Asn Ala Gly Lys Glu Met Ser Arg Leu Ala Arg Leu Val Ile Ile Ala
530                 535                 540 caa aag ttg ggg gag gag gaa att gca ggc aag ctg aat gac aag ctg    1739
Gln Lys Leu Gly Glu Glu Glu Ile Ala Gly Lys Leu Asn Asp Lys Leu
545                 550                 555                 560 gtg gcg tac ctc agt gtc tgg ctt gac tac aag tcc gca aac ccc ctt    1787
Val Ala Tyr Leu Ser Val Trp Leu Asp Tyr Lys Ser Ala Asn Pro Leu
                565                 570                 575 ctg tac gac aag tcc tgg ggc gga atg gtg tct tgt gga tgc agc tac    1835
Leu Tyr Asp Lys Ser Trp Gly Gly Met Val Ser Cys Gly Cys Ser Tyr
            580                 585                 590 gtt tgg ctg gaa cag gag aag aag gcg cgc tgt tcc aac aat gcc aag    1883
Val Trp Leu Glu Gln Glu Lys Lys Ala Arg Cys Ser Asn Asn Ala Lys
        595                 600                 605 tat ttt gag tgc cct gtt ctg cgg gac gtg aat gct gat ttc ggg aac    1931
Tyr Phe Glu Cys Pro Val Leu Arg Asp Val Asn Ala Asp Phe Gly Asn
610                 615                 620 ggg cat tac aac gac cac cat ttc cac tac ggc tac ttc cta tac gcc    1979
Gly His Tyr Asn Asp His His Phe His Tyr Gly Tyr Phe Leu Tyr Ala
625                 630                 635                 640 gca gcc atc gcc gcc cat gta aac ccg gcg tgg ggg aag acg tac aac    2027
Ala Ala Ile Ala Ala His Val Asn Pro Ala Trp Gly Lys Thr Tyr Asn
                645                 650                 655 gag aaa atg ctg ctg ctc ctg cgg gac atc gcc aac ccc aac cgc gac    2075
Glu Lys Met Leu Leu Leu Leu Arg Asp Ile Ala Asn Pro Asn Arg Asp
            660                 665                 670 gac cct tat ttc ccg cag ttc cgg cac ttc gac tgg tac ctc ggc cac    2123
Asp Pro Tyr Phe Pro Gln Phe Arg His Phe Asp Trp Tyr Leu Gly His
        675                 680                 685 tcg tgg gcg tcg ggc atc gtc agc agc ccc aac ggc aag aac cag gag    2171
Ser Trp Ala Ser Gly Ile Val Ser Ser Pro Asn Gly Lys Asn Gln Glu
690                 695                 700 tcc acg tcg gag gca gtg aac gcc cat ttc ggc atc tac ctg tac ggg    2219
Ser Thr Ser Glu Ala Val Asn Ala His Phe Gly Ile Tyr Leu Tyr Gly
705                 710                 715                 720 ctg gca acc aac cac aaa ccc ctt tcc gag atg ggg gag gcg ctg ctc    2267
Leu Ala Thr Asn His Lys Pro Leu Ser Glu Met Gly Glu Ala Leu Leu
                725                 730                 735 ctg atg gaa gca cac agc agc aaa tat tac tgg tac ggg gct ggg ggc    2315
Leu Met Glu Ala His Ser Ser Lys Tyr Tyr Trp Tyr Gly Ala Gly Gly
            740                 745                 750
```

| | | |
|---|---|---|
| gtc ttc ccc gac gag tac cag cac cac atg gcc ggc atc gtc cat gac<br>Val Phe Pro Asp Glu Tyr Gln His His Met Ala Gly Ile Val His Asp<br>     755                    760                   765 | 2363 | |
| ctc ctc ttc gag ttc cag acc tat ttc ggg ccc cag acc tac ttc gtt<br>Leu Leu Phe Glu Phe Gln Thr Tyr Phe Gly Pro Gln Thr Tyr Phe Val<br>     770                    775                   780 | 2411 | |
| cat ggc atc cac gtg ctc ccc ctg acg ggg gcc acc cag ttc ctg ctg<br>His Gly Ile His Val Leu Pro Leu Thr Gly Ala Thr Gln Phe Leu Leu<br>785                    790                   795                   800 | 2459 | |
| tcc ccc gac tgg gtc gcg aag tcc atc cgg acg ttc gac gcc gcc tgc<br>Ser Pro Asp Trp Val Ala Lys Ser Ile Arg Thr Phe Asp Ala Ala Cys<br>                   805                   810                   815 | 2507 | |
| gag gcg gac tcg ttc tgc ctc ggc agc ggc ttc atc acg ttc gcc cac<br>Glu Ala Asp Ser Phe Cys Leu Gly Ser Gly Phe Ile Thr Phe Ala His<br>               820                    825                   830 | 2555 | |
| gcc tcc cgg gct ttc ctg gac aag gac gtc gca tgg gac cga ctg gcg<br>Ala Ser Arg Ala Phe Leu Asp Lys Asp Val Ala Trp Asp Arg Leu Ala<br>             835                    840                   845 | 2603 | |
| gca ctg ccg gac cag ggg ccg ttc aac gtg ttc gac atc ggc tcc ggg<br>Ala Leu Pro Asp Gln Gly Pro Phe Asn Val Phe Asp Ile Gly Ser Gly<br>850                    855                   860 | 2651 | |
| ggc ggc aac ggg aac agc aag acc agc acg ctg ttc tgg tgc gcc tcc<br>Gly Gly Asn Gly Asn Ser Lys Thr Ser Thr Leu Phe Trp Cys Ala Ser<br>865                    870                   875                   880 | 2699 | |
| ctc ggc aac gac gcg gcg ccg ccg atg gac gcg tac ttc cag gac acg<br>Leu Gly Asn Asp Ala Ala Pro Pro Met Asp Ala Tyr Phe Gln Asp Thr<br>                   885                   890                   895 | 2747 | |
| ccc acc gcc gtg gcc cgg cac cgc cgg cgg acg gcc gag cgg tgg ctg<br>Pro Thr Ala Val Ala Arg His Arg Arg Arg Thr Ala Glu Arg Trp Leu<br>     900                    905                   910 | 2795 | |
| gca gta ctg gcg gtg gtg gcc ctc gcc tgt gcc gcg acg tgg tac aca<br>Ala Val Leu Ala Val Val Ala Leu Ala Cys Ala Ala Thr Trp Tyr Thr<br>     915                    920                   925 | 2843 | |
| cgg cag cgg cag ccg gag gcg ttc gac cgc gtg ggc cgg gag ctg aac<br>Arg Gln Arg Gln Pro Glu Ala Phe Asp Arg Val Gly Arg Glu Leu Asn<br>     930                    935                   940 | 2891 | |
| cac agc ttc gcg cag gtg aac cag agc ttc gtg gag ccc gcg cgg ctg<br>His Ser Phe Ala Gln Val Asn Gln Ser Phe Val Glu Pro Ala Arg Leu<br>945                    950                   955                   960 | 2939 | |
| tgg ggc acg atg cgg tac acc gag gtg cgg ggc tac ttc cag ggc tac<br>Trp Gly Thr Met Arg Tyr Thr Glu Val Arg Gly Tyr Phe Gln Gly Tyr<br>                   965                   970                   975 | 2987 | |
| cac acc ctg gac tga gggcggcctg gcctgccatt ctgccgtact caacttccct<br>His Thr Leu Asp<br>                   980 | 3042 | |
| tttgcttgcg ctgaacttgt tggcgtcacg tggcaaccac ctggtcgcac cctaaaaaaa | 3102 | |
| aaaaaaaaaa aaaaaaa | 3119 | |

```
<210> SEQ ID NO 4
<211> LENGTH: 980
<212> TYPE: PRT
<213> ORGANISM: Euglena gracilis Z

<400> SEQUENCE: 4

Met Arg Trp Val Leu Pro Leu Cys Leu Ala Leu Leu Ser Ala Pro Gly
1               5                   10                  15

Thr Ala Asp Leu Cys Thr Tyr Phe Ala Arg Gln Arg Leu Val Asp Phe
            20                  25                  30
```

-continued

```
Pro Asp Val Leu Val Met Pro Val Pro Asp Asn Ala Ala Cys Cys Gly
         35                  40                  45
Val Cys Leu Ala Thr Pro Ala Cys Thr Val Ser Val Leu Thr Asn Thr
 50                  55                  60
Ser Cys His Leu Lys Arg Phe Asn Met Thr Val Asp Asn Lys Thr Leu
 65                  70                  75                  80
Arg Ala Asp Pro Asn Ser Val Val Cys Val Pro Leu Pro Lys Pro Gly
                 85                  90                  95
Gln Gly Pro Ala Gly Ala Ser Tyr Pro Pro Leu Pro Lys Pro Thr Ile
             100                 105                 110
Arg Asp Asn Ala Thr Phe Pro Ala Ala Ser Arg Leu Asp Ser Gly Phe
             115                 120                 125
Pro Arg Leu Ser Met Glu Asn Pro Glu Lys Leu Gly Phe Pro Gly Ile
 130                 135                 140
Ala Arg Asp Gly Phe Ala Ala Pro Asn Val Asp Lys Met Cys Leu Pro
 145                 150                 155                 160
Lys Gly Arg Pro Phe Pro Leu Pro Thr Asn Asp Trp Trp Val Pro Ile
                 165                 170                 175
Ile Arg Pro Thr Pro Glu Thr Thr Leu Asn Tyr Ile Phe Pro Val Pro
             180                 185                 190
Tyr Ile Tyr Asp Met Phe Pro Ala Gly Phe His Leu Ala Tyr Pro Phe
             195                 200                 205
Ile Ile Thr Ser Pro Asn Ser Val Arg Asn Ile Ile Asn Arg Tyr Trp
             210                 215                 220
Thr Val Thr Ala Glu Gly Ala Asp Glu Ala Ser Ser Tyr Cys Val
 225                 230                 235                 240
Arg His Phe Asp Glu Leu Thr Ala Thr Val Ala Trp Arg Ala Thr Thr
                 245                 250                 255
Asn Gln Ser Met Met Glu Met Pro Ile Val Arg Gly Ser Pro Tyr Ala
             260                 265                 270
Thr Val Lys Tyr Phe Gln Ala Gln Pro Lys Leu Ser Thr Ala Gln Lys
             275                 280                 285
Val Arg Ala Phe Phe Val Asp Gly Val Arg Arg Asn Cys Ser Gly Asp
 290                 295                 300
Ser Phe Pro Gly His Lys Phe Thr Val Trp Leu Leu Asp Ser Asp Glu
 305                 310                 315                 320
Glu Trp Gln Phe Trp Val Pro Pro Gly Thr Pro Val Val Cys Gln Val
                 325                 330                 335
Ala Val Glu Arg Gly Met Pro Ala Val Val Ser Val Ala Asp Pro
             340                 345                 350
Ala Phe Ser Gly Trp Val Arg Leu Ala Leu Ser Asn Asn Cys Thr Thr
             355                 360                 365
Gly Met Val Pro Pro Ser Pro His Cys Val Gln Glu Gly Met Ala Asn
 370                 375                 380
Glu Asp Met Glu Asp Tyr Ser Gln Ala Leu Asp Thr Gly Ser Asn Ala
 385                 390                 395                 400
Cys Pro Met Lys Gly Lys Val Gly Met Arg Ala Thr Gly Arg Gln Met
                 405                 410                 415
Glu Tyr Ile Leu Glu Trp Glu Val Ala His Cys Trp Ser Pro Ser Phe
             420                 425                 430
Phe Gln Ser Ser Ser Leu Leu Leu Ile Ala Leu Pro His His Met Ala
             435                 440                 445
```

```
Lys Met Gln Asp Gly Phe Thr Lys Ile Val Pro Thr Gly Gly His Arg
450                     455                 460

Asn Thr Arg Gly Tyr Asn Thr Pro Val Gln Thr Pro His Asn Arg Trp
465                 470                 475                 480

Val Leu Glu Ile Gln Arg Thr Ala Leu Gly Trp Val Glu Thr Pro Asp
                485                 490                 495

Ala Arg Arg Leu Asp Phe Leu Arg Thr Tyr Leu Val Asn Asn Asp Ser
            500                 505                 510

His Phe Asp Leu Pro Pro Asp Val Gln Arg Gly Tyr Ile Asp Pro Tyr
            515                 520                 525

Asn Ala Gly Lys Glu Met Ser Arg Leu Ala Arg Leu Val Ile Ile Ala
530                 535                 540

Gln Lys Leu Gly Glu Glu Ile Ala Gly Lys Leu Asn Asp Lys Leu
545                 550                 555                 560

Val Ala Tyr Leu Ser Val Trp Leu Asp Tyr Lys Ser Ala Asn Pro Leu
                565                 570                 575

Leu Tyr Asp Lys Ser Trp Gly Gly Met Val Ser Cys Gly Cys Ser Tyr
            580                 585                 590

Val Trp Leu Glu Gln Glu Lys Lys Ala Arg Cys Ser Asn Asn Ala Lys
            595                 600                 605

Tyr Phe Glu Cys Pro Val Leu Arg Asp Val Asn Ala Asp Phe Gly Asn
            610                 615                 620

Gly His Tyr Asn Asp His His Phe His Tyr Gly Tyr Phe Leu Tyr Ala
625                 630                 635                 640

Ala Ala Ile Ala Ala His Val Asn Pro Ala Trp Gly Lys Thr Tyr Asn
                645                 650                 655

Glu Lys Met Leu Leu Leu Arg Asp Ile Ala Asn Pro Asn Arg Asp
                660                 665                 670

Asp Pro Tyr Phe Pro Gln Phe Arg His Phe Asp Trp Tyr Leu Gly His
            675                 680                 685

Ser Trp Ala Ser Gly Ile Val Ser Ser Pro Asn Gly Lys Asn Gln Glu
    690                 695                 700

Ser Thr Ser Glu Ala Val Asn Ala His Phe Gly Ile Tyr Leu Tyr Gly
705                 710                 715                 720

Leu Ala Thr Asn His Lys Pro Leu Ser Glu Met Gly Glu Ala Leu Leu
                725                 730                 735

Leu Met Glu Ala His Ser Ser Lys Tyr Tyr Trp Tyr Gly Ala Gly Gly
            740                 745                 750

Val Phe Pro Asp Glu Tyr Gln His His Met Ala Gly Ile Val His Asp
            755                 760                 765

Leu Leu Phe Glu Phe Gln Thr Tyr Phe Gly Pro Gln Thr Tyr Phe Val
            770                 775                 780

His Gly Ile His Val Leu Pro Leu Thr Gly Ala Thr Gln Phe Leu Leu
785                 790                 795                 800

Ser Pro Asp Trp Val Ala Lys Ser Ile Arg Thr Phe Asp Ala Ala Cys
                805                 810                 815

Glu Ala Asp Ser Phe Cys Leu Gly Ser Gly Phe Ile Thr Phe Ala His
            820                 825                 830

Ala Ser Arg Ala Phe Leu Asp Lys Asp Val Ala Trp Asp Arg Leu Ala
            835                 840                 845

Ala Leu Pro Asp Gln Gly Pro Phe Asn Val Phe Asp Ile Gly Ser Gly
850                 855                 860
```

```
Gly Gly Asn Gly Asn Ser Lys Thr Ser Thr Leu Phe Trp Cys Ala Ser
865                 870                 875                 880

Leu Gly Asn Asp Ala Ala Pro Pro Met Asp Ala Tyr Phe Gln Asp Thr
                885                 890                 895

Pro Thr Ala Val Ala Arg His Arg Arg Thr Ala Glu Arg Trp Leu
            900                 905                 910

Ala Val Leu Ala Val Val Ala Leu Ala Cys Ala Ala Thr Trp Tyr Thr
            915                 920                 925

Arg Gln Arg Gln Pro Glu Ala Phe Asp Arg Val Gly Arg Glu Leu Asn
                930                 935                 940

His Ser Phe Ala Gln Val Asn Gln Ser Phe Val Glu Pro Ala Arg Leu
945                 950                 955                 960

Trp Gly Thr Met Arg Tyr Thr Glu Val Arg Gly Tyr Phe Gln Gly Tyr
                965                 970                 975

His Thr Leu Asp
            980

<210> SEQ ID NO 5
<211> LENGTH: 2756
<212> TYPE: DNA
<213> ORGANISM: Euglena gracilis Z
<220> FEATURE:
<221> NAME/KEY: CDS
<222> LOCATION: (49)..(2667)

<400> SEQUENCE: 5
gaaaacactt tctgagtgtc tattttttt cgcatatggt gcgccgcc atg ccg gct      57
                                                   Met Pro Ala
                                                   1 gtt gcc gcg ccg ccg ccc acc ccc gcg ggg cgg cgg tgg ccc ctg ctg     105
Val Ala Ala Pro Pro Pro Thr Pro Ala Gly Arg Arg Trp Pro Leu Leu
 5                  10                  15 ctg gcg ctg tgc ctc tgc gtg ccc gcg gcg ctg gcg ccg ccc gcg gtg     153
Leu Ala Leu Cys Leu Cys Val Pro Ala Ala Leu Ala Pro Pro Ala Val
20                  25                  30                  35 ccc gcg gta cct ccc ctg tcc acc cgg gac cct gtg gct gag ggc ttt     201
Pro Ala Val Pro Pro Leu Ser Thr Arg Asp Pro Val Ala Glu Gly Phe
                40                  45                  50 gac ggc ttc gcg cga gaa ggg ccc cac gcg ccg ctg gcg gag cgg ctg     249
Asp Gly Phe Ala Arg Glu Gly Pro His Ala Pro Leu Ala Glu Arg Leu
            55                  60                  65 tgc ttc gcc gac aag cgc cgg gcc ctt ccc acc cac aag tgg tgg ctg     297
Cys Phe Ala Asp Lys Arg Arg Ala Leu Pro Thr His Lys Trp Trp Leu
        70                  75                  80 ccg ctg gtc cgc ccc cgc ccg agg gcc ggc cgg ccc ctc ctg gtg cag     345
Pro Leu Val Arg Pro Arg Pro Arg Ala Gly Arg Pro Leu Leu Val Gln
85                  90                  95 ctg ccg tac atc atc cac gtc cag gac acg ggg ctg gaa gtg tac tac     393
Leu Pro Tyr Ile Ile His Val Gln Asp Thr Gly Leu Glu Val Tyr Tyr
100                 105                 110                 115 ccc cac gtg aag gca acc gcc cac aca gtg cag aat gtc atc ccc gac     441
Pro His Val Lys Ala Thr Ala His Thr Val Gln Asn Val Ile Pro Asp
                120                 125                 130 gct cca tct tgg cac atc acc tgc aag cgt act cag ccg tat tgt gtg     489
Ala Pro Ser Trp His Ile Thr Cys Lys Arg Thr Gln Pro Tyr Cys Val
            135                 140                 145 cgg gat gcg gac gag ttc atg gtg cgc att gtt tgg ggt gac gtg ttg     537
Arg Asp Ala Asp Glu Phe Met Val Arg Ile Val Trp Gly Asp Val Leu
        150                 155                 160
```

```
gat gtg acc ctt gtc agg ggt tcg ccg tac atc aac gtc ttc tcg cag        585
Asp Val Thr Leu Val Arg Gly Ser Pro Tyr Ile Asn Val Phe Ser Gln
    165                 170                 175 ggg gtg gcg ttg aag gtt aac tcc ccg acg ccg atc agc cac ctg ctg        633
Gly Val Ala Leu Lys Val Asn Ser Pro Thr Pro Ile Ser His Leu Leu
180                 185                 190                 195 gtc ggc agc ctg ccg tac ttc tgc ggc gtg cag agc gac cca gcg cgg        681
Val Gly Ser Leu Pro Tyr Phe Cys Gly Val Gln Ser Asp Pro Ala Arg
                200                 205                 210 gtg ttc aag gtg gag ctg cgg ggc gag gag gag tgg acg gtc ttc aca        729
Val Phe Lys Val Glu Leu Arg Gly Glu Glu Glu Trp Thr Val Phe Thr
    215                 220                 225 gac tcg gac atc cga ttg caa tgc gat ccg att gcg aac ggg ctc agt        777
Asp Ser Asp Ile Arg Leu Gln Cys Asp Pro Ile Ala Asn Gly Leu Ser
230                 235                 240 act tca gag cat ttc ttc ggc ctc atc cgc ctt gcc ttg tcg aat aac        825
Thr Ser Glu His Phe Phe Gly Leu Ile Arg Leu Ala Leu Ser Asn Asn
    245                 250                 255 tgt acg tcg cat ggg aag ctg gag gcc cgg gat gac aac ccc cac tgt        873
Cys Thr Ser His Gly Lys Leu Glu Ala Arg Asp Asp Asn Pro His Cys
260                 265                 270                 275 ggg ccg tgg tcc ggg cac ctc ggg ggc tat gcc aag gct ctt ctg gag        921
Gly Pro Trp Ser Gly His Leu Gly Gly Tyr Ala Lys Ala Leu Leu Glu
                280                 285                 290 ggc agc cag acg tgc acg cgg ggc ggc acg cag gtc agc acg gcg ctg        969
Gly Ser Gln Thr Cys Thr Arg Gly Gly Thr Gln Val Ser Thr Ala Leu
    295                 300                 305 ctc cct gac ggg gcg cgg gcc atc gtc cac tgg agc ctg tac tcc tgc       1017
Leu Pro Asp Gly Ala Arg Ala Ile Val His Trp Ser Leu Tyr Ser Cys
310                 315                 320 tgg gcg ccg ctg cgc tcc cag gcc gag gcc ccc gtg ggc aag ctg atg       1065
Trp Ala Pro Leu Arg Ser Gln Ala Glu Ala Pro Val Gly Lys Leu Met
    325                 330                 335 atg acg gcg ctg ccc cac cac ctg ccc ctg ttc gac ggg aac acg acg       1113
Met Thr Ala Leu Pro His His Leu Pro Leu Phe Asp Gly Asn Thr Thr
340                 345                 350                 355 gca gtg gtg ggt ggg gga cat cgc aac ctg cgg ggt tgg gta tct ggg       1161
Ala Val Val Gly Gly Gly His Arg Asn Leu Arg Gly Trp Val Ser Gly
                360                 365                 370 gtc ctg acg acg ggc agc cac tgg gtt ctc tcc atc cgc cac cca gac       1209
Val Leu Thr Thr Gly Ser His Trp Val Leu Ser Ile Arg His Pro Asp
    375                 380                 385 gtt gca tgg ttg gaa ccg cct gat cgc ttc agt cgg aac act acg ctg       1257
Val Ala Trp Leu Glu Pro Pro Asp Arg Phe Ser Arg Asn Thr Thr Leu
390                 395                 400 aaa gcc ttc aaa ggc gcg tcc ccg acg gac aag gcc gcg gac atg cat       1305
Lys Ala Phe Lys Gly Ala Ser Pro Thr Asp Lys Ala Ala Asp Met His
    405                 410                 415 tat gac ctg ccc cgc ccc gcg gcg gag ggc ttc gtg gag tgc tac ccg       1353
Tyr Asp Leu Pro Arg Pro Ala Ala Glu Gly Phe Val Glu Cys Tyr Pro
420                 425                 430                 435 gcg ggc cgc ctg ctg gcg cgg ctg gcg acg ctg gtc cag gtg ggg gag       1401
Ala Gly Arg Leu Leu Ala Arg Leu Ala Thr Leu Val Gln Val Gly Glu
                440                 445                 450 ctg ctg ggg gag gcc aag gcg gcc cag ggc ctg ttg tcc cgg ctg acg       1449
Leu Leu Gly Glu Ala Lys Ala Ala Gln Gly Leu Leu Ser Arg Leu Thr
    455                 460                 465 cag cac ttc tcc ctg tgg ctg gac cac cgg gct aag aac cgg ctc gtc       1497
Gln His Phe Ser Leu Trp Leu Asp His Arg Ala Lys Asn Arg Leu Val
470                 475                 480
```

-continued

| | |
|---|---|
| tat gac cag agc tgg ggc ggt ctc att gcg tgc ggc atc tcc tcc ggc<br>Tyr Asp Gln Ser Trp Gly Gly Leu Ile Ala Cys Gly Ile Ser Ser Gly<br>485                    490                    495 | 1545 |
| tgg tac cag agt gcg gct gat tgc cca acg ttg gag gag ccg ggc act<br>Trp Tyr Gln Ser Ala Ala Asp Cys Pro Thr Leu Glu Glu Pro Gly Thr<br>500                    505                510                515 | 1593 |
| gag ttt ggg agc tcg ctc ttc aac gac cac cat ttt cat tat ggc tat<br>Glu Phe Gly Ser Ser Leu Phe Asn Asp His His Phe His Tyr Gly Tyr<br>              520                525                530 | 1641 |
| ttt ata tat gtt gcg gct gtc atc gcc aag ttc aat cgg aag tgg gcg<br>Phe Ile Tyr Val Ala Ala Val Ile Ala Lys Phe Asn Arg Lys Trp Ala<br>535                    540                    545 | 1689 |
| tcg gca tac cgc gag aag gtg ctg acg ctg atc cgg gac atc gcc aac<br>Ser Ala Tyr Arg Glu Lys Val Leu Thr Leu Ile Arg Asp Ile Ala Asn<br>              550                555                560 | 1737 |
| ccc agc ccg cag gac ccg cat ttc ccg ccg tac cgc cat ttc gac tgg<br>Pro Ser Pro Gln Asp Pro His Phe Pro Pro Tyr Arg His Phe Asp Trp<br>565                    570                    575 | 1785 |
| tac acc ggc cac tcc tgg gcg tcc tcc ggc ctc gct acc gac ccc tat<br>Tyr Thr Gly His Ser Trp Ala Ser Ser Gly Leu Ala Thr Asp Pro Tyr<br>580                    585                    590                595 | 1833 |
| ggt ctt cgg cag gag gca agc agc gag gct ctt cat gcc tgg ttc agc<br>Gly Leu Arg Gln Glu Ala Ser Ser Glu Ala Leu His Ala Trp Phe Ser<br>              600                605                610 | 1881 |
| atc tac ctt tac ggc ctc gct gtg gag gac gag acc gtg cag gct ctg<br>Ile Tyr Leu Tyr Gly Leu Ala Val Glu Asp Glu Thr Val Gln Ala Leu<br>615                    620                    625 | 1929 |
| ggg aag gcc atg ctc ttg atg gag gcc cac agc acg aac ttc tac tgg<br>Gly Lys Ala Met Leu Leu Met Glu Ala His Ser Thr Asn Phe Tyr Trp<br>              630                635                640 | 1977 |
| cgg gtc cat aac gcc acg gtg gtg tac ccg aag ctg tac gag cac cgg<br>Arg Val His Asn Ala Thr Val Val Tyr Pro Lys Leu Tyr Glu His Arg<br>645                    650                    655 | 2025 |
| ctg gtc ggg gcg ctg cag gag atg cgg gtg gag tcc cac gcc tcc tcc<br>Leu Val Gly Ala Leu Gln Glu Met Arg Val Glu Ser His Ala Ser Ser<br>660                    665                670                675 | 2073 |
| ggg cag cgg gac ttc ctg ctg tac ggg gcc cag ctc agc ccc atc gcg<br>Gly Gln Arg Asp Phe Leu Leu Tyr Gly Ala Gln Leu Ser Pro Ile Ala<br>              680                685                690 | 2121 |
| ccc cac gtc ctg ctg acc tcc ccg ctg cca tgg gcc gtg gac gcg tac<br>Pro His Val Leu Leu Thr Ser Pro Leu Pro Trp Ala Val Asp Ala Tyr<br>695                    700                    705 | 2169 |
| cac gac ttc cgc cgg tcc tgt gcg gcg gat gag gag tgc gaa gac acc<br>His Asp Phe Arg Arg Ser Cys Ala Ala Asp Glu Glu Cys Glu Asp Thr<br>              710                715                720 | 2217 |
| ggc act gtg gcc gcg ttg gcc gcc cac cag gca ctg ttg gat cgg gac<br>Gly Thr Val Ala Ala Leu Ala Ala His Gln Ala Leu Leu Asp Arg Asp<br>725                    730                    735 | 2265 |
| gcg gcg tgg gag ttc gcc acg gac ctg ccg ggg gac gtg ttc tcc gac<br>Ala Ala Trp Glu Phe Ala Thr Asp Leu Pro Gly Asp Val Phe Ser Asp<br>740                    745                    750                755 | 2313 |
| acg tgc gcg gtg ggc gct gcg acc agc cgc acg gcg ctg ctg cac ttc<br>Thr Cys Ala Val Gly Ala Ala Thr Ser Arg Thr Ala Leu Leu His Phe<br>              760                765                770 | 2361 |
| atc ggg gcg tat ggc gcc ggg gag aag gtg gtg gac ctc ggg gag gag<br>Ile Gly Ala Tyr Gly Ala Gly Glu Lys Val Val Asp Leu Gly Glu Glu<br>              775                780                785 | 2409 |
| gcc gtg ccg ctg aag ccc cgc ggc ggg cac cgg tgg ctg gtg gtc gtg<br>Ala Val Pro Leu Lys Pro Arg Gly Gly His Arg Trp Leu Val Val Val<br>790                    795                    800 | 2457 |

```
ttc ggg gta gcg ctg gcc ttc ggc ggc ctc atc ggc tac gag gcc ttt    2505
Phe Gly Val Ala Leu Ala Phe Gly Gly Leu Ile Gly Tyr Glu Ala Phe
805                 810                 815 gcc aaa gcc cgg ctg cac ctc gag gag cga cgc tcg tta ctg gcc ccc    2553
Ala Lys Ala Arg Leu His Leu Glu Glu Arg Arg Ser Leu Leu Ala Pro
820                 825                 830                 835 gcc tcc ccg ccc cag gag ctg atg ccc cgc atc cag ctg gac ggc acc    2601
Ala Ser Pro Pro Gln Glu Leu Met Pro Arg Ile Gln Leu Asp Gly Thr
                840                 845                 850 gca gac gcc gac ccc ggt gta ccg gcc tac ggc acg gag gac ggc cct    2649
Ala Asp Ala Asp Pro Gly Val Pro Ala Tyr Gly Thr Glu Asp Gly Pro
            855                 860                 865 ccg gag ctc ggg ggc tga ctgtgccggg gaggggggtg acctccacgt           2697
Pro Glu Leu Gly Gly
            870 gcaccaggga tttccaccac tgccgcacgc aaaaaaaaaa aaaaaaaaaa aaaaaaaa    2756

<210> SEQ ID NO 6
<211> LENGTH: 872
<212> TYPE: PRT
<213> ORGANISM: Euglena gracilis Z

<400> SEQUENCE: 6

Met Pro Ala Val Ala Ala Pro Pro Thr Pro Ala Gly Arg Arg Trp
1               5                   10                  15

Pro Leu Leu Leu Ala Leu Cys Leu Cys Val Pro Ala Ala Leu Ala Pro
            20                  25                  30

Pro Ala Val Pro Ala Val Pro Pro Leu Ser Thr Arg Asp Pro Val Ala
        35                  40                  45

Glu Gly Phe Asp Gly Phe Ala Arg Glu Gly Pro His Ala Pro Leu Ala
    50                  55                  60

Glu Arg Leu Cys Phe Ala Asp Lys Arg Ala Leu Pro Thr His Lys
65                  70                  75                  80

Trp Trp Leu Pro Leu Val Arg Pro Arg Pro Arg Ala Gly Arg Pro Leu
                85                  90                  95

Leu Val Gln Leu Pro Tyr Ile Ile His Val Gln Asp Thr Gly Leu Glu
            100                 105                 110

Val Tyr Tyr Pro His Val Lys Ala Thr Ala His Thr Val Gln Asn Val
        115                 120                 125

Ile Pro Asp Ala Pro Ser Trp His Ile Thr Cys Lys Arg Thr Gln Pro
    130                 135                 140

Tyr Cys Val Arg Asp Ala Asp Glu Phe Met Val Arg Ile Val Trp Gly
145                 150                 155                 160

Asp Val Leu Asp Val Thr Leu Val Arg Gly Ser Pro Tyr Ile Asn Val
                165                 170                 175

Phe Ser Gln Gly Val Ala Leu Lys Val Asn Ser Pro Thr Pro Ile Ser
            180                 185                 190

His Leu Leu Val Gly Ser Leu Pro Tyr Phe Cys Gly Val Gln Ser Asp
        195                 200                 205

Pro Ala Arg Val Phe Lys Val Glu Leu Arg Gly Glu Glu Trp Thr
    210                 215                 220

Val Phe Thr Asp Ser Asp Ile Arg Leu Gln Cys Asp Pro Ile Ala Asn
225                 230                 235                 240

Gly Leu Ser Thr Ser Glu His Phe Phe Gly Leu Ile Arg Leu Ala Leu
                245                 250                 255
```

```
Ser Asn Asn Cys Thr Ser His Gly Lys Leu Glu Ala Arg Asp Asn
            260                 265                 270

Pro His Cys Gly Pro Trp Ser Gly His Leu Gly Gly Tyr Ala Lys Ala
        275                 280                 285

Leu Leu Glu Gly Ser Gln Thr Cys Thr Arg Gly Gly Thr Gln Val Ser
        290                 295                 300

Thr Ala Leu Leu Pro Asp Gly Ala Arg Ala Ile Val His Trp Ser Leu
305                 310                 315                 320

Tyr Ser Cys Trp Ala Pro Leu Arg Ser Gln Ala Glu Ala Pro Val Gly
                325                 330                 335

Lys Leu Met Met Thr Ala Leu Pro His His Leu Pro Leu Phe Asp Gly
            340                 345                 350

Asn Thr Thr Ala Val Val Gly Gly His Arg Asn Leu Arg Gly Trp
        355                 360                 365

Val Ser Gly Val Leu Thr Thr Gly Ser His Trp Val Leu Ser Ile Arg
        370                 375                 380

His Pro Asp Val Ala Trp Leu Glu Pro Pro Asp Arg Phe Ser Arg Asn
385                 390                 395                 400

Thr Thr Leu Lys Ala Phe Lys Gly Ala Ser Pro Thr Asp Lys Ala Ala
                405                 410                 415

Asp Met His Tyr Asp Leu Pro Arg Pro Ala Ala Glu Gly Phe Val Glu
                420                 425                 430

Cys Tyr Pro Ala Gly Arg Leu Leu Ala Arg Leu Ala Thr Leu Val Gln
                435                 440                 445

Val Gly Glu Leu Leu Gly Glu Ala Lys Ala Ala Gln Gly Leu Leu Ser
450                 455                 460

Arg Leu Thr Gln His Phe Ser Leu Trp Leu Asp His Arg Ala Lys Asn
465                 470                 475                 480

Arg Leu Val Tyr Asp Gln Ser Trp Gly Gly Leu Ile Ala Cys Gly Ile
                485                 490                 495

Ser Ser Gly Trp Tyr Gln Ser Ala Ala Asp Cys Pro Thr Leu Glu Glu
                500                 505                 510

Pro Gly Thr Glu Phe Gly Ser Ser Leu Phe Asn Asp His His Phe His
            515                 520                 525

Tyr Gly Tyr Phe Ile Tyr Val Ala Ala Val Ile Ala Lys Phe Asn Arg
            530                 535                 540

Lys Trp Ala Ser Ala Tyr Arg Glu Lys Val Leu Thr Leu Ile Arg Asp
545                 550                 555                 560

Ile Ala Asn Pro Ser Pro Gln Asp Pro His Phe Pro Pro Tyr Arg His
                565                 570                 575

Phe Asp Trp Tyr Thr Gly His Ser Trp Ala Ser Ser Gly Leu Ala Thr
            580                 585                 590

Asp Pro Tyr Gly Leu Arg Gln Glu Ala Ser Ser Glu Ala Leu His Ala
            595                 600                 605

Trp Phe Ser Ile Tyr Leu Tyr Gly Leu Ala Val Glu Asp Glu Thr Val
            610                 615                 620

Gln Ala Leu Gly Lys Ala Met Leu Leu Met Glu Ala His Ser Thr Asn
625                 630                 635                 640

Phe Tyr Trp Arg Val His Asn Ala Thr Val Val Tyr Pro Lys Leu Tyr
                645                 650                 655

Glu His Arg Leu Val Gly Ala Leu Gln Glu Met Arg Val Glu Ser His
            660                 665                 670
```

```
Ala Ser Ser Gly Gln Arg Asp Phe Leu Leu Tyr Gly Ala Gln Leu Ser
            675                 680                 685

Pro Ile Ala Pro His Val Leu Leu Thr Ser Pro Leu Pro Trp Ala Val
690                 695                 700

Asp Ala Tyr His Asp Phe Arg Arg Ser Cys Ala Ala Asp Glu Glu Cys
705                 710                 715                 720

Glu Asp Thr Gly Thr Val Ala Ala Leu Ala Ala His Gln Ala Leu Leu
                725                 730                 735

Asp Arg Asp Ala Ala Trp Glu Phe Ala Thr Asp Leu Pro Gly Asp Val
            740                 745                 750

Phe Ser Asp Thr Cys Ala Val Gly Ala Ala Thr Ser Arg Thr Ala Leu
            755                 760                 765

Leu His Phe Ile Gly Ala Tyr Gly Ala Gly Glu Lys Val Val Asp Leu
        770                 775                 780

Gly Glu Glu Ala Val Pro Leu Lys Pro Arg Gly Gly His Arg Trp Leu
785                 790                 795                 800

Val Val Val Phe Gly Val Ala Leu Ala Phe Gly Gly Leu Ile Gly Tyr
                805                 810                 815

Glu Ala Phe Ala Lys Ala Arg Leu His Leu Glu Glu Arg Arg Ser Leu
                820                 825                 830

Leu Ala Pro Ala Ser Pro Pro Gln Glu Leu Met Pro Arg Ile Gln Leu
            835                 840                 845

Asp Gly Thr Ala Asp Ala Asp Pro Gly Val Pro Ala Tyr Gly Thr Glu
        850                 855                 860

Asp Gly Pro Pro Glu Leu Gly Gly
865                 870

<210> SEQ ID NO 7
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 7
tcctgacaga ggcaaacttg cccatc                                        26

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 8
gatgggcaag tttgcctctg tcagga                                        26

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 9
ggagcagcgc ctcccccatc tcggaaag                                      28
```

```
<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 10
cttgtggatg cagctacgtt tggctgg                                          27

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 11
tggtcgttga agagcgagct cccaaac                                          27

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 12
cacccagacg ttgcatggtt ggaaccg                                          27

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 13
ttagtgatgg tgatggtggt gatggctagg                                       30
```